US007194916B2

(12) United States Patent
Ouellet et al.

(10) Patent No.: US 7,194,916 B2
(45) Date of Patent: Mar. 27, 2007

(54) APPARATUS AND METHOD FOR TESTING STIFFNESS OF ARTICLES

(75) Inventors: Jean-Claude Ouellet, St-Jean-Port-Joli (CA); Jean Campagna, St-Nicolas (CA); Danick Dupont, Quebec (CA); Gratien Beauchemin, Quebec (CA); Jacques Labbé, Sainte-Foy (CA)

(73) Assignee: Centre de recherche industrielle du Quebec, Sainte-Foy (CA)

( * ) Notice: Subject to any disclaimer, the term of this patent is extended or adjusted under 35 U.S.C. 154(b) by 260 days.

(21) Appl. No.: 10/427,964

(22) Filed: May 2, 2003

(65) Prior Publication Data

US 2003/0226404 A1 Dec. 11, 2003

(30) Foreign Application Priority Data

May 2, 2002 (CA) .................................. 2384553

(51) Int. Cl.
*G01N 3/20* (2006.01)
(52) U.S. Cl. ....................................................... 73/852
(58) Field of Classification Search ................. 73/851, 73/852, 853, 855, 849
See application file for complete search history.

(56) References Cited

U.S. PATENT DOCUMENTS

| 3,158,021 A | 11/1964 | Walters et al. | |
| 3,196,672 A | 7/1965 | Keller | |
| 4,289,037 A | 9/1981 | Vinopal | |
| 4,463,607 A * | 8/1984 | Hilton | ......................... 73/587 |
| 4,589,288 A | 5/1986 | Porter et al. | |
| 4,708,020 A | 11/1987 | Lau et al. | |
| 5,503,024 A * | 4/1996 | Bechtel et al. | ................. 73/852 |
| 5,564,573 A * | 10/1996 | Palm et al. | ............. 73/862.451 |
| 5,699,274 A * | 12/1997 | Starostovic, Jr. | ............. 73/849 |

(Continued)

FOREIGN PATENT DOCUMENTS

WO WO 01/38849 A1 5/2001

*Primary Examiner*—Max Noori
(74) *Attorney, Agent, or Firm*—Jean-Claude Boudreau

(57) ABSTRACT

An apparatus for testing stiffness characteristics such as modulus of elasticity E of an article such as a piece of lumber moving in a conveying direction transverse to the testing axis, comprises a bearing unit capable of contacting the piece of lumber at two spaced apart portions thereof. There is provided a first deflecting unit including a first working element being normally disposed in a first static position relative to the conveying path for applying a first thrust against a loaded area on the article at an intermediary portion thereof located between the spaced apart portions, to produce an article deflection of a first magnitude. Each working element defines a loading surface extending substantially parallel to the article-conveying path. There is further provided a second deflecting unit including a second working element being normally disposed in a second static position relative to the conveying path for applying a second thrust against a loaded area of the article intermediary portion, to produce an article deflection of a second magnitude, wherein the second position differs from the first position relative to the conveying path by a differential value. The apparatus further comprises load cells coupled to the bearing unit for generating signals indicative of respective magnitudes the first and second thrusts as applied by first and second deflecting units, and a computer for deriving from such signals and differential value an indication of the stiffness of the article, such as modulus of elasticity E.

36 Claims, 22 Drawing Sheets

U.S. PATENT DOCUMENTS

| | | |
|---|---|---|
| 5,804,738 A | 9/1998 | Bach et al. |
| 5,892,157 A * | 4/1999 | Syre .......................... 73/812 |
| 6,053,052 A * | 4/2000 | Starostovic ................. 73/851 |
| 6,055,867 A * | 5/2000 | Dunne et al. ................. 73/849 |
| 6,381,546 B1 * | 4/2002 | Starostovic ................. 73/849 |

* cited by examiner

Fig-12

MSR Demo-E.Vi

Parameters | Correction Factors

Modulus of Elasticity Correction Factors

| Average E | Correction Static E 2x3 | Correction Static E Edge 2x4 | Correction Dynamic E |
|---|---|---|---|
| 1400000 | 0.978 | 0.982 | 1.100 |
| 1500000 | 0.946 | 0.964 | 1.100 |
| 1600000 | 0.936 | 0.958 | 1.100 |
| 1700000 | 0.925 | 0.951 | 1.100 |
| 1800000 | 0.913 | 0.945 | 1.100 |
| 1900000 | 0.903 | 0.939 | 1.100 |
| 2000000 | 0.892 | 0.933 | 1.100 |
| 2400000 | 0.848 | 0.908 | 1.100 |

Enter password to modify parameters
*****
119

OK

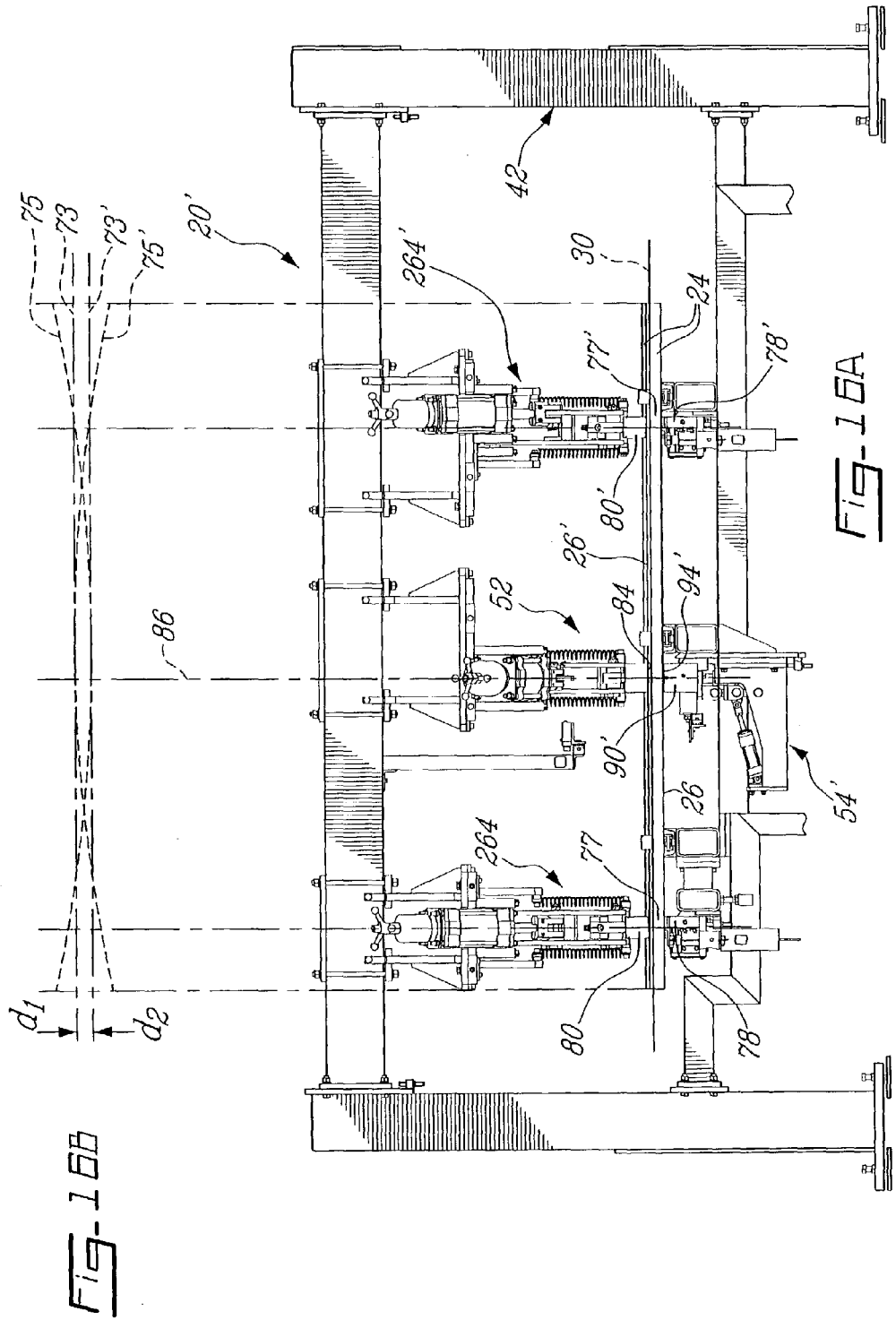

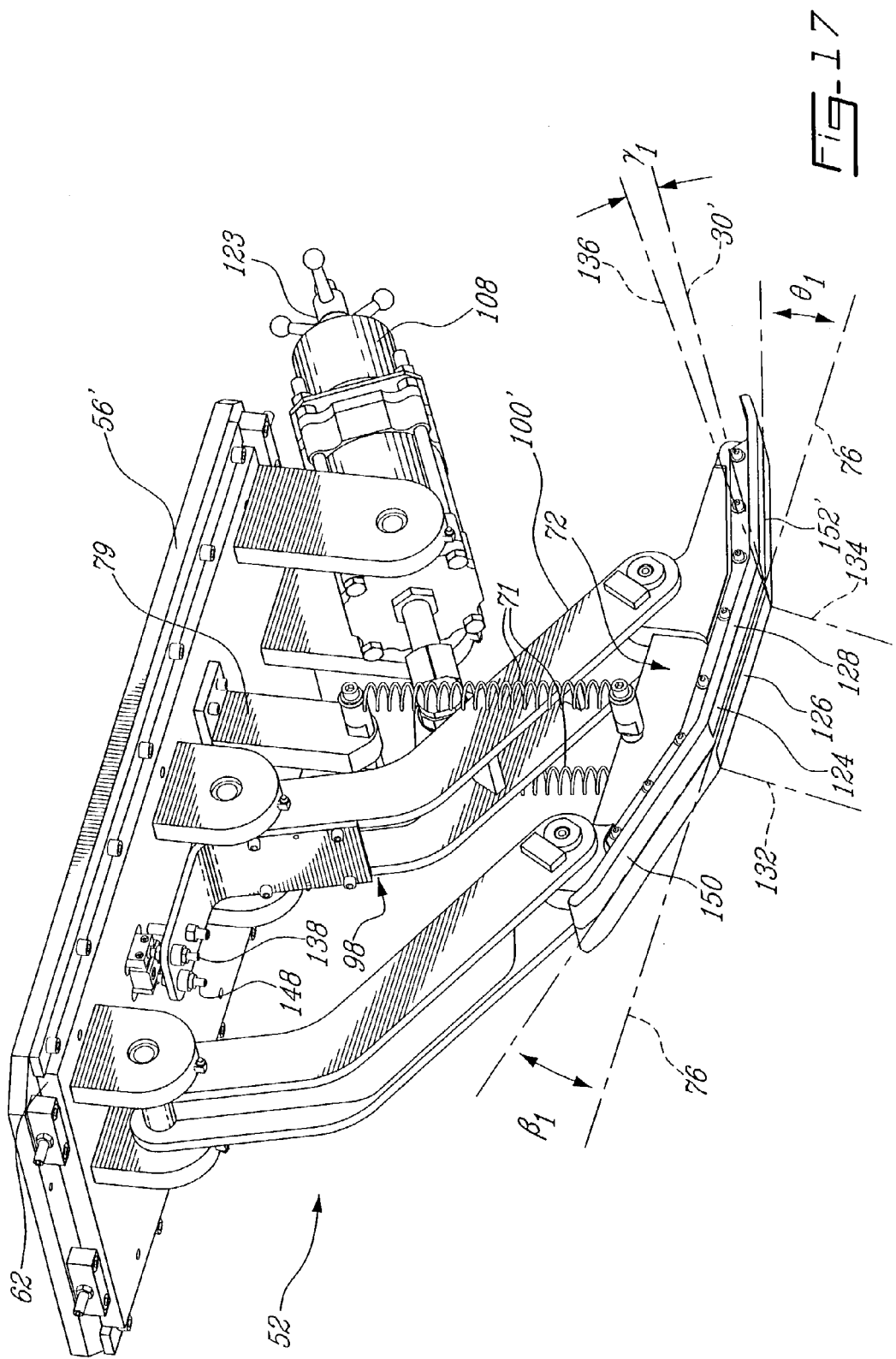

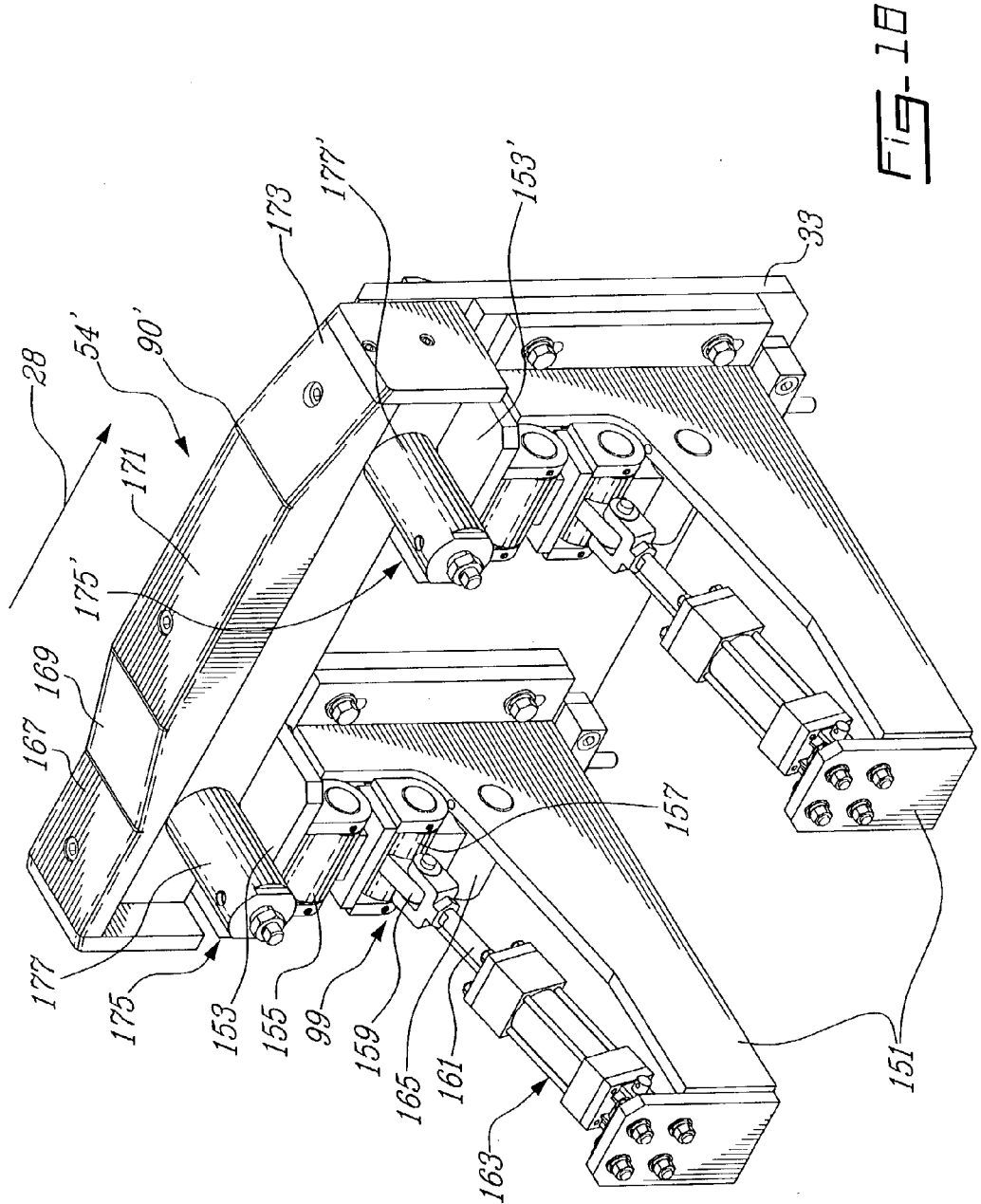

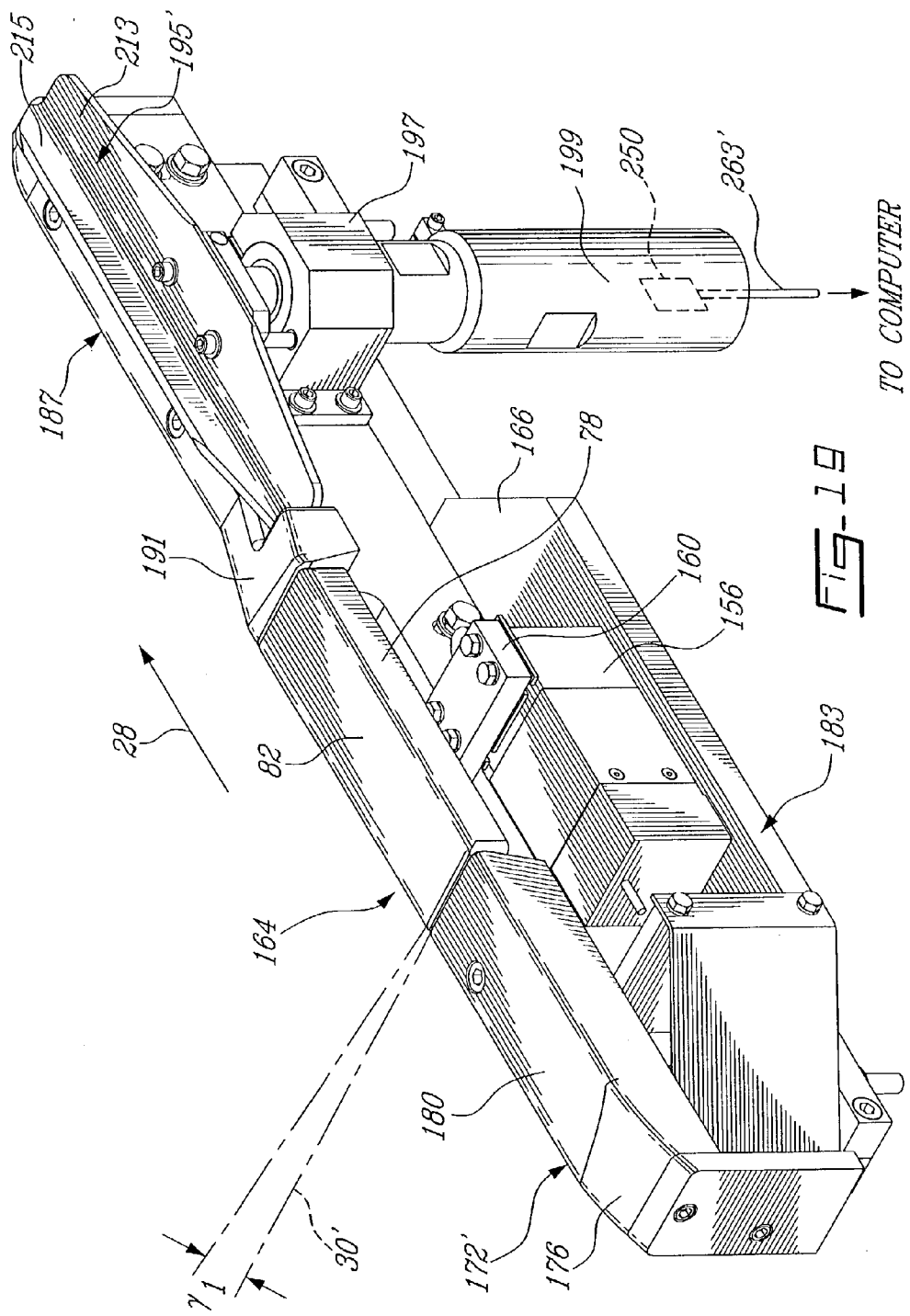

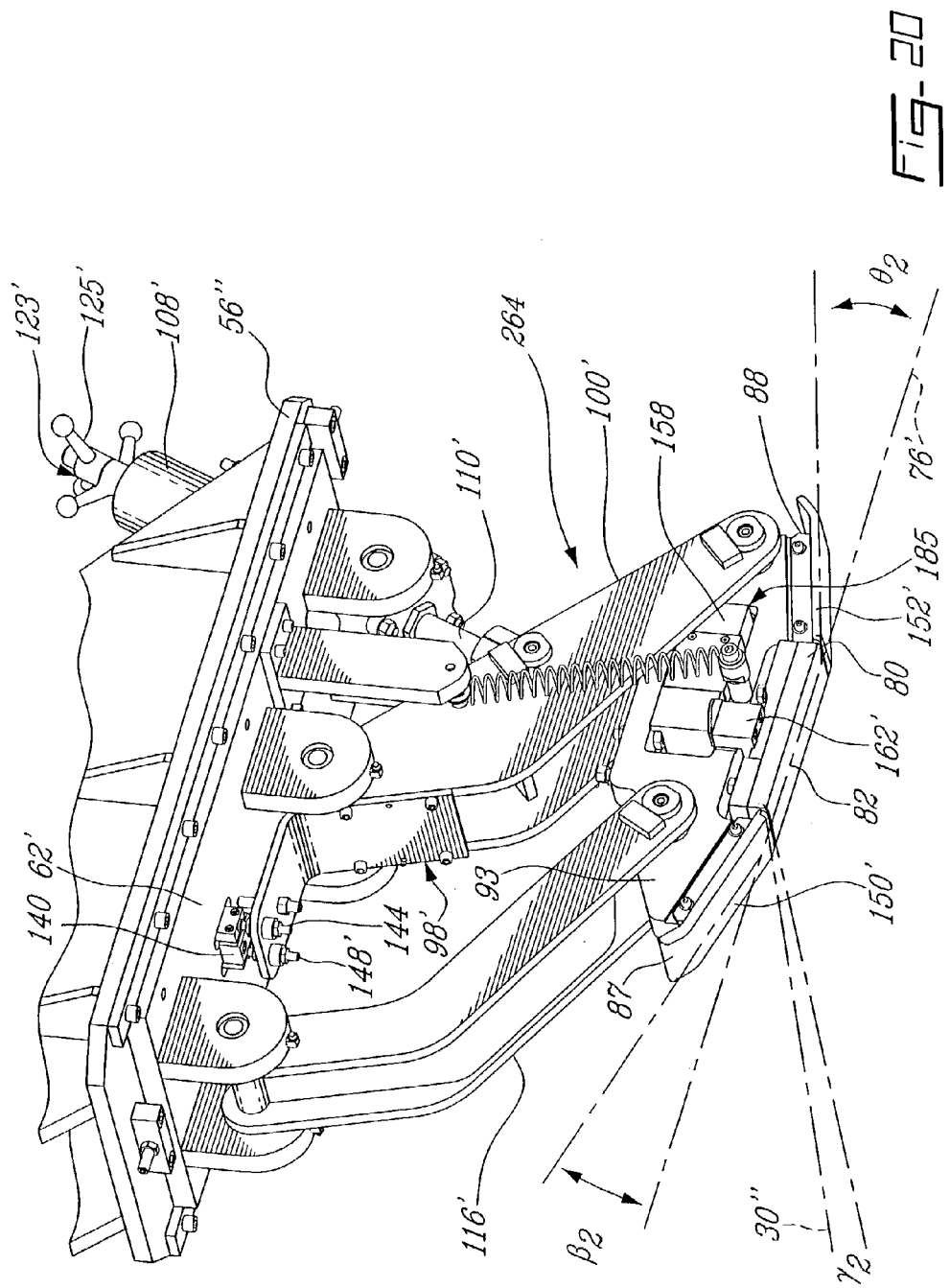

APPARATUS AND METHOD FOR TESTING STIFFNESS OF ARTICLES

FIELD OF THE INVENTION

The present invention relates generally to the field of structural products testing, and more particularly to apparatus and methods for the testing of stiffness of such products, and is particularly useful for carrying out Machine Stress Rating (MSR) tests for the purpose of grading lumber according to stiffness characteristics.

BRIEF DESCRIPTION OF THE BACKGROUND ART

Over the past years, stiffness testing of structural products has been widely used in manufacturing and building industries as an important quality concern warranting security of use of these products in the field. Stiffness characteristics of structural products are usually tested through the measurement of a parameter known as modulus of elasticity (E) also known as Young modulus, which is essentially defined as the ratio of the magnitude of a load applied to the article over the magnitude of the corresponding deformation induced to the same article as a result of the applied load. In the lumber processing industry, stiffness measurement is usually performed as part of a standard quality testing procedure known as Machine Stress Rating (MSR) in addition to the assessment of other lumber characteristics such as geometric and surface features, to comply with the requirements of specific applications such as I-beams for flooring and roof truss structures. Typically, the measured modulus of elasticity value for each piece of lumber is compared to reference threshold of increasing values associated with increasing quality of lumber, so as to assign a corresponding grade to each piece of lumber tested.

A first approach to measure the stiffness of lumber consists of using a static testing bench wherein the piece of lumber is disposed on two spaced apart support elements while a load of a predetermined magnitude is applied onto an area of the piece of lumber located between the two support elements, for measuring the corresponding deflection induced. Such basic approach is employed by the apparatus disclosed in U.S. Pat. No. 4,589,288 issued to Porter et al on May 20, 1986 which makes use of two series of parallel rolls for laterally supporting a wood panel to be tested and a loading bar capable of applying a linear load at a center area of the panel and transversally thereto, by means of a two-way cylinder for sequentially applying a first load magnitude followed by a second load of an incremented magnitude, which load magnitudes are chosen so as to involve a substantially linear portion of the deflection curve characterizing the tested panel. The applied load magnitudes are measured with a load cell and the extension or distance moved by the cylinder in applying the incremental load is either predetermined or measured in real-time. A similar testing approach is also used by the system disclosed in U.S. Pat. No. 6,053,052 issued to Starostovic on Apr. 25, 2000. Although such static approach has become considered in the wood processing industry as a standard procedure whose results are widely employed as reference values according to which MSR grades are established, in the context of on-line quality procedures, its use is limited to the testing of sampled pieces coming from the production line, and cannot be implemented as a real-time, dynamic testing procedure for all pieces being processed while they are conveyed through the production line.

A second, dynamic approach for carrying out stiffness testing consists of measuring the modulus of elasticity E of a piece of lumber while it is conveyed lengthwise, typically downstream from a lumber planer. Such dynamic stiffness testing approach is used by the apparatus disclosed in U.S. Pat. No. 3,196,672 issued to Keller on Jul. 27, 1965, which apparatus includes first and second series of rolls between which is disposed a load-measuring roll in such a manner to impart a predetermined deflection to the piece of lumber passing thereon. A third series of rolls at a location downstream from the first load-measuring roll, and a second load-measuring roll disposed between the second and third series of rolls are used to impart a second predetermined deflection onto an opposed face of the piece of lumber as compared to the face onto which the first deflection is imparted. The opposed deflection removes the effect of bow and warp naturally present in the piece of lumber. Load measurement signals are then integrated as the piece of lumber is passing through the apparatus, and a main value as an estimation of the modulus of elasticity E of the entire piece of lumber is obtained.

A similar dynamic stiffness measurement approach involving longitudinal piece conveying is also employed by the apparatus disclosed in U.S. Pat. No. 5,503,024 issued to Bechtel et al on Apr. 2, 1996, and in U.S. Pat. No. 5,564,573 issued to Palm et al on Oct. 15, 1996. While representing an improvement over the static testing approach as to the capability of these prior dynamic testing apparatus to systematically test all pieces of lumber as they are processed in the production line, the use of such apparatus is limited to industrial installations where there is sufficient available space within the production line to receive these prior art apparatus whose dimensions generally exceed the length of the longer piece of lumber to be processed.

A variant of above-mentioned dynamic stiffness testing approach is disclosed is U.S. Pat. No. 4,289,037 issued to Vinopal on Sep. 15, 1981 which describes a system making use of a conveyer for transporting wood pieces lengthwise through a first roll-based load applying device used to apply a transversal load on a central area of the wood piece located between two supporting rolls to induce a corresponding longitudinal deflection of the wood piece, means for measuring respective magnitudes of the applied load and the induced deflection, a second roll-based device for applying a load of a second magnitude on the same area of the wood piece, means for measuring respective magnitude of the second load and second corresponding deflection induced on the wood piece, and a computer for classifying the tested wood piece according to load and deflection magnitudes and to assign a grade accordingly. A similar approach for on-line stiffness testing of wood panels is disclosed in U.S. Pat. No. 5,804,738 (CA 2,220,789) issued to Bach et al on Sep. 8, 1998. The use of roll-based load applying device as taught by the above-mentioned prior patents is associated with problems related to load measurement signals stability which adversely affects consistency and reliability of stiffness estimation. The fact that a load applying roll is characterized by a loading surface that is limited to a peripheral portion of its circumference adjacent the loaded surface of the article in the conveying direction yields to such load measurement signal stability problems, especially in cases where significant vibration occurs when the article is transported on the conveyer. The ultimate effect of this limitation is to yield inconsistent stiffness estimation that may result to classification errors such as under-grading or over-grading of pieces of lumber.

An alternative approach that has been developed to comply with minimum space requirement consists of measuring stiffness characteristics while each piece of lumber is conveyed along a path in a direction parallel to the transverse dimension of the piece of lumber. Such approach is employed by the apparatus disclosed in U.S. Pat. No. 3,158,021 issued to Walters et al on Nov. 24, 1964, according to which limit bending stress of wood pieces are measured using a transverse conveyer provided on a loading station making use of two parallel lever-mounted weights disposed over the transverse conveyer so as to distribute a corresponding load onto a central area of each wood piece transversally conveyed. Such prior art apparatus carrying out a single load measurement corresponding to a single deflection measurement to obtain the desired bending stress limit measurement, the significant influence of bow and warp that are naturally present on most pieces of lumber cannot be adequately compensated according to the proposed technique.

There is still a need for testing stiffness apparatus and methods which advantageously comply with minimum space requirements imposed by industrial users of stiffness testing system, while ensuring enhanced load measurement signals stability to provide reliable and consistent stiffness estimation.

BRIEF SUMMARY OF THE INVENTION

It is therefore a main object of the present invention to provide apparatus and method for testing stiffness of an article that allow compact implementation while providing reliable stiffness estimation.

According to the above-mentioned object, from a broad aspect, there is provided an apparatus for testing stiffness of an elongate article such as a piece of lumber along a predetermined testing axis associated therewith, the article having first and second opposed surfaces aligned with the conveying path in a predetermined conveying position. The apparatus comprises transport means for moving the article along a predetermined path through the apparatus in a conveying direction substantially transverse to said testing axis. The apparatus further comprises at least one article bearing unit capable of contacting at least the first article surface at two spaced apart portions of the article, and a first deflecting unit including a first working element capable of being disposed in a first, substantially static position relative to the article conveying path and cooperating with the article bearing unit for applying a first thrust against a loaded area of the second article surface at an intermediary portion located between the spaced apart portions of the article as it moves transversely through the apparatus, to produce an article deflection of a first magnitude extending along a first deflection axis perpendicular to the conveying direction and the testing axis. The apparatus further comprises a second deflecting unit including a second working element capable of being disposed in a second, substantially static position relative to the article conveying path and cooperating with the article bearing unit for applying a second thrust against a loaded area of the first article surface at the intermediary portion of the article as it further moves transversely through the apparatus, to produce an article deflection of a second magnitude opposite to the first deflection magnitude and extending along a second deflection axis substantially parallel to the first deflection axis. The apparatus further comprises at least one load measuring unit capable of generating signals indicative of respective magnitudes of the first and second thrusts, and a data processing device for deriving an indication of the stiffness of the article from the opposed deflection magnitudes and thrust indicative signals. Furthermore, each working element defines a loading surface extending substantially parallel to the article conveying path when disposed in its respective substantially static position, thereby maximizing transverse load distribution over the loaded area, for enhanced load measurement signals stability and more reliable and consistent stiffness estimation.

According to the above-mentioned object, from a further broad aspect of the invention, there is provided a method for testing stiffness of an article along a predetermined testing axis while the article moves along a predetermined path in a conveying direction substantially transverse to the testing axis, the article having first and second opposed surfaces aligned with the conveying path in a predetermined conveying position. The method comprises the steps of: i) contacting the first article surface at two spaced apart portions of the article while applying a first thrust against a loaded area of the second article surface at an intermediary portion located between the spaced apart portions of the article as it moves along the conveying path, to produce an article deflection of a first magnitude extending along a first deflection axis perpendicular to the conveying direction and the testing axis; ii) contacting the first article surface at two spaced apart portions of the article while applying a second thrust against a loaded area of the second article surface at the intermediary portion of the article as it further moves along the conveying path, to produce an article deflection of a second magnitude extending along a second deflection axis substantially parallel to the first deflection axis, the second position differing from the first position relative to the conveying path by a predetermined differential value; iii) measuring respective magnitudes of the first and second thrusts; and iv) deriving an indication of the stiffness of the article from the differential value and the thrust magnitudes; wherein each loaded area substantially extends over the whole transverse dimension of the article while the thrust magnitudes are measured.

According to the above-mentioned object, from another broad aspect of the invention, there is provided a method for testing stiffness of an elongate article along a predetermined testing axis, the article having first and second opposed surfaces aligned with the conveying path in a predetermined conveying position. The method comprises the steps of: i) moving the article along a predetermined path in a conveying direction substantially transverse to said testing axis; ii) contacting the first article surface at two spaced apart portions of the article while applying a first thrust against a loaded area of the second article surface at an intermediary portion located between the spaced apart portions of the article as it moves transversely along the conveying path, to produce an article deflection of a first magnitude extending along a first deflection axis perpendicular to the conveying direction and the testing axis; iii) measuring the magnitude of said first thrust; iv) contacting the second article surface at two spaced apart portions of the article while applying a second thrust against a loaded area of the first article surface at the intermediary portion of the article as it further moves transversely along the conveying path, to produce an article deflection of a second magnitude opposite to said first deflection magnitude and extending along a second deflection axis substantially parallel to the first deflection axis; v) measuring the magnitude of the second thrust; and vi) deriving an indication of the stiffness of the article from the opposed deflection magnitudes and the thrust magnitudes.

BRIEF DESCRIPTION OF THE DRAWINGS

Preferred embodiments of an apparatus and method for testing stiffness of an article according to the invention will now be described in detail in view of the accompanying drawings in which:

FIG. 12 is a representation of a typical screen displayed while the apparatus is in the parameter setting mode regarding correction factors for modulus of elasticity E.

FIG. 16A is a partial end view of the second embodiment of FIG. 14;

FIG. 16B is a schematic representation of deflections imparted to a piece of lumber in view of the second embodiment of FIG. 16A;

FIG. 17 is a perspective view of the first deflecting unit provided on the second embodiment of FIG. 14, shown in an extended, thrust-applying position;

FIG. 18 is a perspective view of the second deflecting unit provided on the second embodiment of FIG. 14, shown in deflecting static position;

FIG. 19 is a perspective view of first (right) rail as part of the first article bearing unit, with corresponding load measuring subunit and profile sensing device according to the second embodiment;

FIG. 20 is a perspective view of one of the pushing devices as part of the second article bearing unit provided on the of the second embodiment of FIG. 14, shown in an extended, thrust-applying position;

DETAILED DESCRIPTION OF THE PREFERRED EMBODIMENTS

Figure 1:
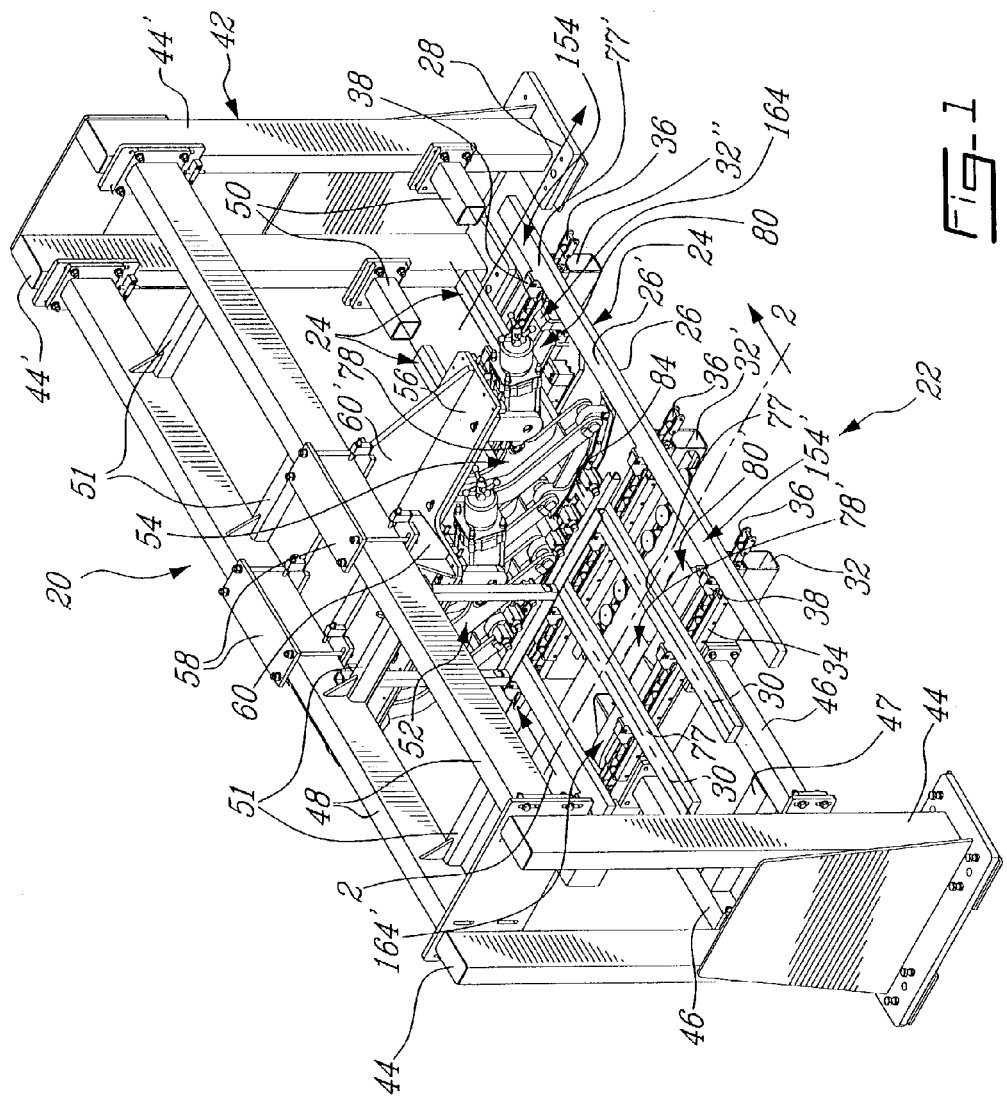
FIG. 1 is a perspective view of the main mechanical components provided on a first preferred embodiment of apparatus according to the present invention.

Referring now to the drawings, preferred embodiments of apparatus and method for testing stiffness of article according to the invention will now be described in detail in the context of a MSR lumber grading application wherein structural pieces of lumber such as studs (2×3, 2×4, etc.) are transversally conveyed through the apparatus of the invention to be assigned a specific MSR grade. However, it is to be understood that the present invention can also be used for testing stiffness of other types of articles such as wood panels or any other kind of boards produced in the lumber processing industry, as well as articles made of other materials that may require stiffness measurement in the context of other industrial fields such as in plastic and metal product manufacturing industries.

Figure 2:
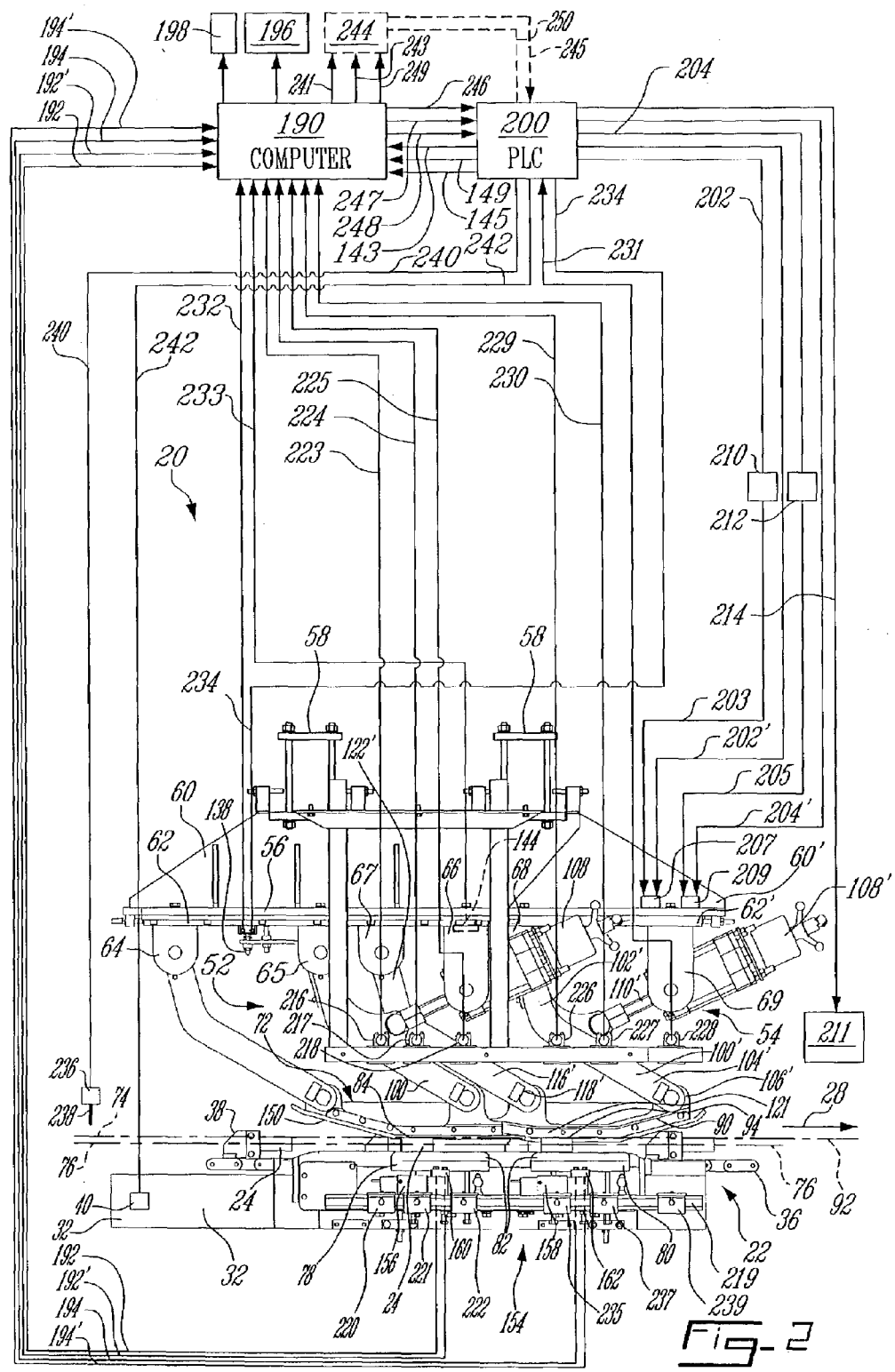
FIG. 2 is a general block diagram of the first embodiment of apparatus according to the invention in relation with a partial cross-sectional elevation view of the main mechanical components according to lines 2—2 of FIG. 1, showing the deflecting units in thrust applying positions on the pieces of lumber under test, with the central conveyor beam being removed to better show details of the right load measuring unit.
Figure 3:
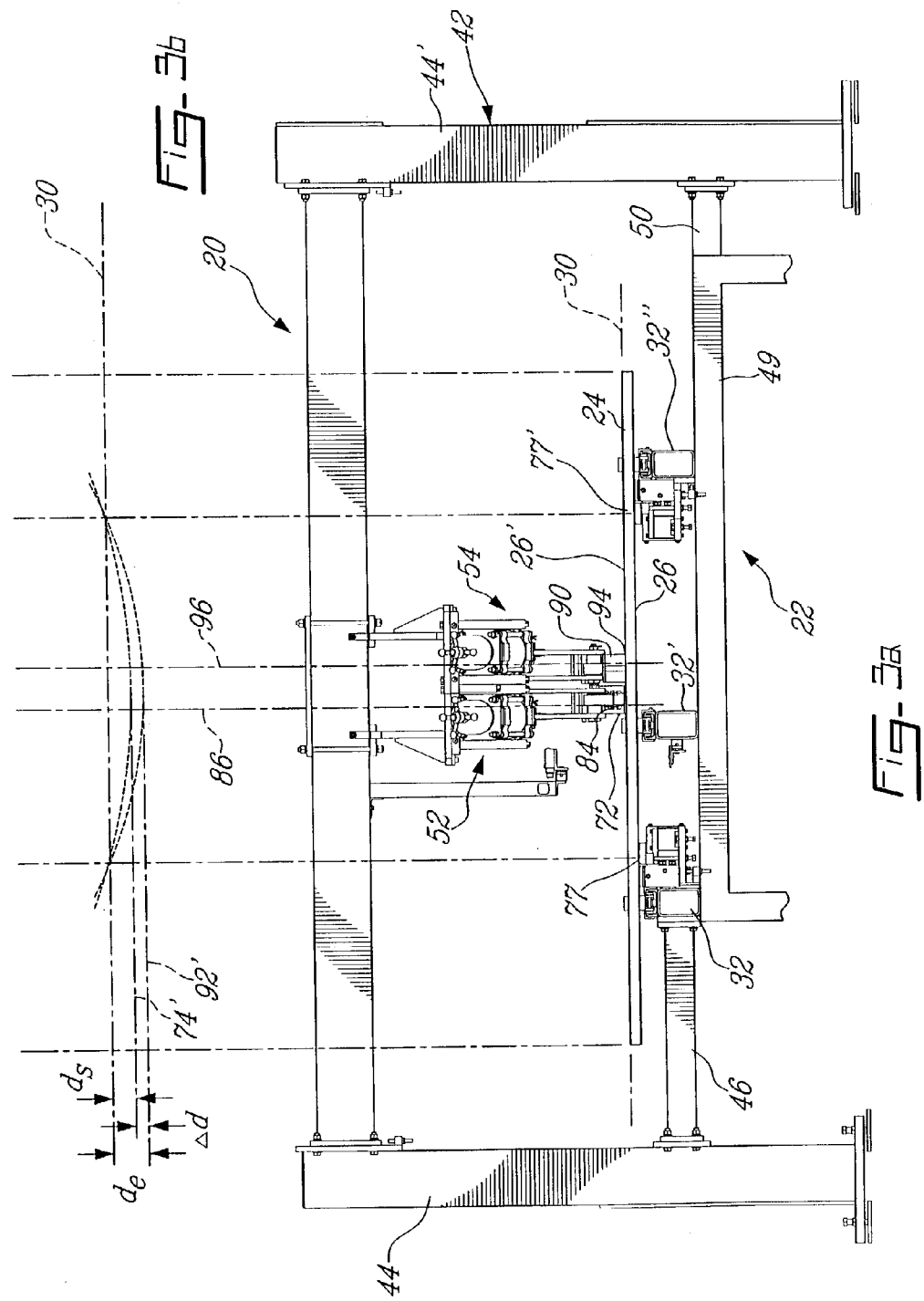
FIG. 3A is a partial end view of the first embodiment of FIG. 1.
FIG. 3B is a schematic representation of deflections imparted to a piece of lumber in view of the first embodiment of FIG. 3A.

Referring now to FIG. 1, the article testing apparatus according to the first preferred embodiment of the invention and as generally designated at 20 is adapted for use with a conventional transverse conveying system generally designated at 22 for transporting a plurality of articles such as pieces of lumber 24 each having opposed main bottom and top surfaces 26, 26', which pieces of lumber 24 move along a predetermined path through apparatus 20 in a conveying direction indicated by arrow 28 substantially transverse to a testing axis 30 associated with each piece of lumber 24 along which stiffness will be estimated as described below. Conveniently, the transverse conveyer system 22 that is used in combination with the stiffness testing apparatus 20 of the invention is an existing conveyer system already present in the processing line, such as used at a transfer station between the output of a planer and downstream a manual grading station. Typically, such transverse conveyer system 22 includes two or more longitudinally extending frame beams 32, 32', 32" onto each of which is mounted a guide rail 34 defining a channel through which a driving chain 36 extends as better shown in FIG. 4. Secured to each chain 36 in a predetermined spaced relationship are a series of transverse catch blocks 38 for driving forward each piece of lumber 24 along the conveying path in direction 28 while maintaining the pieces 24 in a parallel spaced relationship. The conveyor system 22 is also provided with a known driving device (not shown) adjusted to impart movement to the pieces of lumber 24 in a predetermined conveying speed which is typically of about 1 m/s and is also provided with a displacement sensor such as rotary encoder 40 as shown in FIG. 2 for generating a signal indicating article displacement along the conveying direction as will be explained later in more detail. As shown in FIG. 1, the apparatus includes a main frame 42 formed by two pairs of lateral upright columns 44, 44' which are secured one to each other at upper portion thereof with a pair of overhead horizontal beams 48. Overhead horizontal beams 48 are connected to one another using a plurality of link members 51. Each column 44 is secured to a left-side conveyer frame beam 32 using a pair of lateral beams 46 linked by a transverse member 47. In a similar way, while being not illustrated in FIG. 1, each upright columns 44' is secured to the base frame portion 49 of the conveyer system 22 as shown in FIG. 3A, using a pair of right-side lateral beams 50.

Turning back to FIG. 1, the apparatus 20 further includes first and second deflecting units generally designated at 52, 54 as better shown in FIG. 2, which are adjustably secured to the frame overhead beams 48 using an overhead mounting unit having top mounting plates 56 being maintained in a suspended position using a pair of displaceable attachments 58, with a pair of parallel vertical walls 60, 60'. Secured to top mounting plate 56 are first and second bottom mounting plates 62, 62' to which are in turn respectively secured the first and second deflecting units 52, 54, using a plurality of pivot members pairs 64, 65, 66 and 67, 68, 69 attached to bottom mounting plates 62 and 62', respectively. The first deflecting unit 52 includes a first working element 72 capable of being disposed in a first, substantially static position as indicated by axis 74 in FIG. 2 relative to an article conveying path represented by axis 76 and as also presented in FIG. 3B by an axis 74' which is coplanar with axis 74 shown in FIG. 2. The apparatus 20 further includes an article bearing unit including first and second pairs of rails 78, 78' and 80, 80' for contacting the bottom surface 26 of each piece of lumber 24 under test at two spaced apart portions thereof, as better shown in FIG. 1. The rails 78, 78' and 80, 80' define load bearing surfaces extending substantially parallel to the conveying direction indicated by arrow 28, for contacting the bottom surface 26 at spaced apart portions 77, 77' thereof. First and second pairs of rails 78, 78' and 80, 80' are also disposed in a spaced relationship in the same conveying direction 28, whereby their respective load bearing surfaces 82 sequentially receive the bottom surface 26 of each piece of lumber 24 when the latter moves past first and second locations along the conveying path 76 as shown in FIG. 2, at which first and second locations the first and second deflecting units 52, 54 are disposed to face the top surface 26' of each piece of lumber 24 under test.

Referring to FIG. 2 in view of FIG. 1, the first working element 72 when being disposed in the first static position indicated by axis 74 relative to the article conveying path 76 and cooperating with rails 78, 78' of the article bearing unit, is used to apply a first thrust against a loaded area 84 of the top surface 26' of piece of lumber 24 at an intermediary portion located between spaced apart portions 77, 77' as piece of lumber 24 is moving through the apparatus 20, as better shown in FIG. 3A. The thrust applied against loaded area 84 produces a deflection $d_s$ of the piece of lumber 24 of a first magnitude extending along a first deflection axis 86 perpendicular to conveying direction 28 and testing axis 30 as shown in FIG. 1. Turning back to FIG. 2, secured to the bottom mounting plate 62', the second deflecting unit 54 is disposed laterally and adjacent first deflecting unit 52 in a location downstream from the corresponding location of first deflecting unit 52, to receive a piece of lumber 24 leaving the thrust applying area defined by the first working element 72 provided on first deflecting unit 52. The second deflecting unit 54 includes a second working element 90 capable of being disposed in a second, substantially static position indicated by axis 92 in FIG. 2 relative to conveying path 76 and cooperating with rails 80, 80' of the article bearing unit for applying a second thrust against a loaded area 94 of top surface 26' of piece of lumber 24 at intermediary portion thereof between spaced apart portions 77, 77' as the piece of lumber 24 further moves through the apparatus 20, as also represented in FIG. 3B by an axis 92' which is coplanar with axis 92 shown in FIG. 2. The second thrust applied against loaded area 94 produces a deflection $d_l$ of piece of lumber 24 of a second magnitude extending along a second deflection axis 96 substantially parallel to first deflection axis 86. It is pointed out that the schematic deflection representation shown in FIG. 3B employs a scale that has been intentionally amplified as compared with actual deflection imparted to a tested piece of lumber for the purpose of illustration. It can be seen from FIG. 3B that the second position as indicated by axis 74' in which the first working element 72 is disposed differs from the first position of second working element 90 by a differential value Δd associated with a nominal predetermined value $\Delta d_n$ as will be later explained in detail, so that second deflection magnitude $d_l$ differs from first deflection magnitude $d_s$ by this differential value Δd so that:

$$d_l = d_s + \Delta d \quad (1)$$

It is to be understood that according to the first preferred embodiment of the invention, the deflecting unit 52 has been chosen to receive the piece of lumber 24 first so as to produce a deflection of a first magnitude $d_s$ which is smaller than the second larger magnitude $d_l$ obtained when the piece of lumber 24 passes under the second deflecting unit 54 as located downstream from first deflecting unit 52. However, the respective position of first and second working elements 72, 90 may be alternatively set so that the deflection of larger magnitude $d_l$ could be measured first, followed by the measurement of the deflection of smaller magnitude $d_s$. Moreover, while first and second deflecting units 52, 54 are preferably disposed in laterally adjacent locations one to each other so that distinct respective loaded areas 84, 94 are subjected to thrust applied by first and second deflecting units 52, 54, the latter units may alternatively be disposed in alignment one to each other in a spaced apart relationship along the conveying direction so to apply the respective thrust on a same loaded area.

Figure 5:
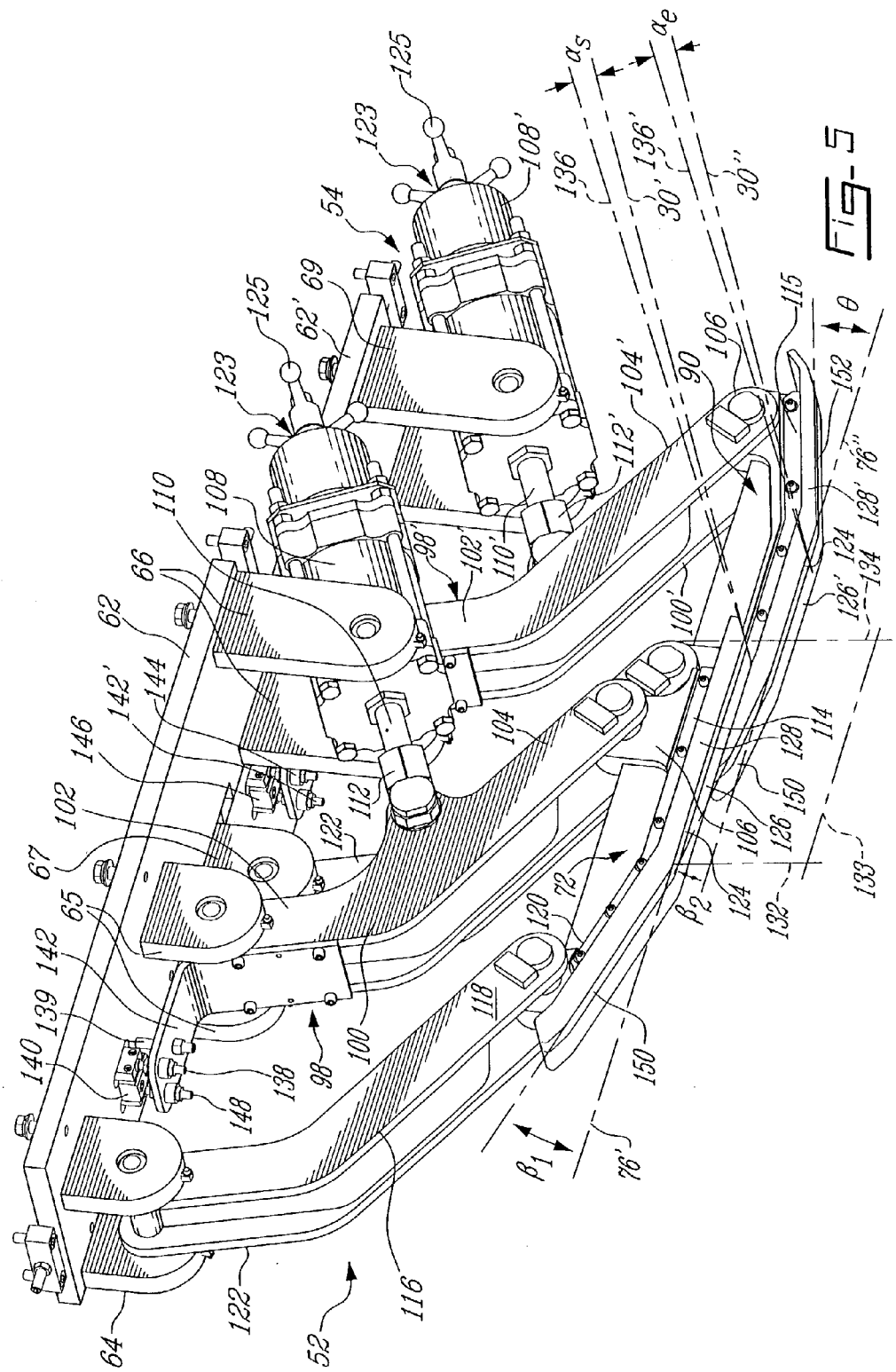
FIG. 5 is a perspective view of the deflecting units of the first embodiment of FIG. 1, shown in an extended, thrust-applying position.
Figure 6:
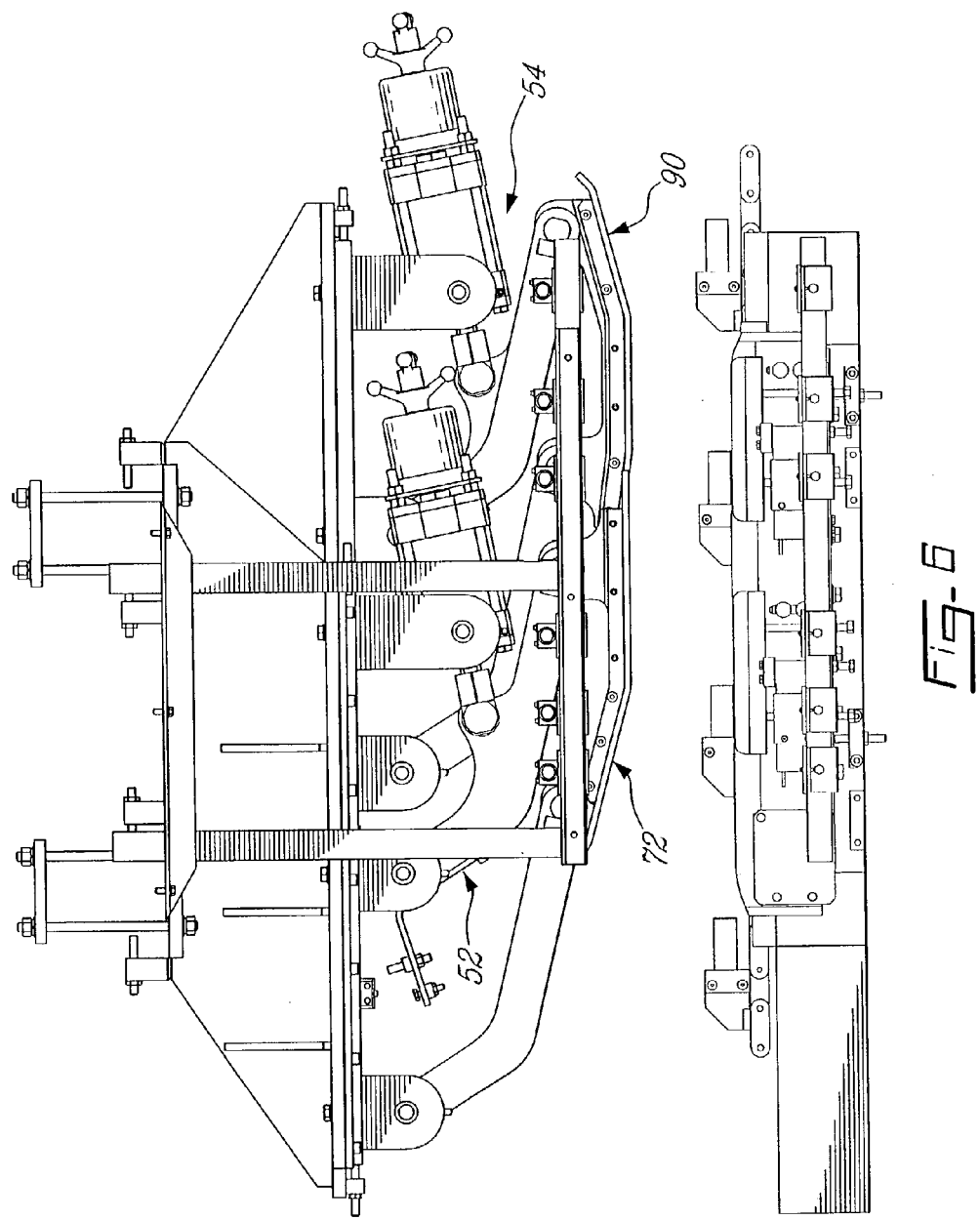
FIG. 6 is a partial cross-sectional elevation view similar than FIG. 3A, showing the deflecting units in a retracted position.

Turning now to FIG. 5, the first deflecting unit 52 further includes a first displaceable mechanism 98 for holding the first working element 72, which mechanism 98 s selectively controllable to move the working element 72 between the first substantially static position indicated by axis 74, 74' in FIGS. 2 and 3B respectively, relative to the conveying path indicated by axis 76 on FIG. 2, and a retracted position as shown in FIG. 6 wherein the first working element 72 is away from the article conveying path to prevent obstruction thereof. The latter function is especially useful for preventing apparatus blockage due to abnormal article position feeding condition such as edge-standing or additional piece of lumber driven by a same catch block, or for performing maintenance tasks. Turning back to FIG. 5 in view of FIG. 2, the first displaceable mechanism 98 includes a lever unit provided with a first double- member 100 having a bearing end 102 pivotally secured to the apparatus frame through pivot member pair 65, first bottom mounting plate 62, top mounting plate 56, wall 60 and displaceable attachments 58. The first double-member 100 further has a working end 104 pivotally connected to the first working element 72 through a further pivot member pair 106. The displaceable mechanism 98 is further provided with an actuator 108 which a preferably a pneumatic linear actuator readily available in the marketplace such as supplied by Gilbert-Tech (Roberval, Quebec, Canada), which actuator 108 is mounted to the apparatus frame through pivot member pair 66 secured to first bottom mounting plate 62 in a same way as pivot member pair 65. The pneumatic actuator 108 is provided with a conventional mechanism 123 for adjusting the limit stroke of piston 110 using a rotary handle 125 provided thereon, allowing accurate adjustment of the first static position, indicated by axis 74, 74' in FIGS. 2 and 3B respectively, of the first working element 72 relative to the conveying path indicated by axis 76 on FIG. 2, in a direction perpendicular to the associated conveying direction 28 and testing axis 30 as shown in FIG. 1. At the end of a linearly displaceable piston 110 provided on actuator 108 is an end coupling element 112 that is pivotally secured to a central portion of first double-member 100 to selectively exert thereon a compression force maintaining the first working element 72 in the first static position as indicated by axis 74 shown in FIGS. 2 and 3B, and to provide the movement of first working element 72 between the position shown in FIGS. 2 and 5 and the retracted position as shown in FIG. 6. The first actuator 108 is capable of exerting the compression force within a compliance range whenever the counteracting force exerted by loaded area 84 onto first working element 72 in reaction of the applied thrust exceeds the rated pressure developed by the pneumatic actuator 108, the value of which being maintained at a preset value as will be later explained in more detail.

Turning again to FIG. 5, the first double-member 100 is pivotally connected to a rear portion 114 of first working element 72, while a second double-member 116 provided on displaceable mechanism 98 has a working end 118 pivotally connected to a front portion 120 of first working element 72, and a bearing end 122 pivotally secured to the apparatus frame through pivot member pair 64 secured to second bottom mounting plate 62 in a same way as pivot member pairs 65 and 66. The first working element 72 defines a loading surface 124 extending substantially parallel to the conveying path as indicated by axis 76 in FIG. 2 when disposed in the first static position as indicated by axis 74, 74' in FIGS. 2 and 3B, respectively. It can be seen from FIG. 5 in view of FIGS. 3A and 3B that the loading surface 124 provided on first working element 72 preferably has first and second symmetrical portions 126, 128 with respect to a transverse plane defined by truncated lines 132, 133 and 134 in FIG. 5 and passing through first deflection axis 86 shown in FIG. 3A. It can be appreciated from FIG. 5 in view of FIGS. 3A and 3B that first and second loading surface portions 126, 128 further extend toward respective spaced apart portions 77, 77' of piece of lumber 24 transversely to the conveying direction according to a symmetrical angle $\alpha_s$ defined by axis 136 on FIG. 5 which extends from surface loading portion 128 and with respect to an axis 30' parallel to testing axis 30 shown in FIG. 3B, which symmetrical angle as being substantially proportional to the first deflection magnitude $d_s$ along axis 86 of FIGS. 3A and 3B, which is parallel to axis 132, 134 shown in FIG. 5. For a given transverse span between rails 78, 78' as shown in FIG. 1, which is typically of about 6 feet for a 10-feet piece of lumber, symmetrical angle $\alpha_s$ will have a value of about 1°. As shown in FIG. 5, such angular requirement in respect of first and second symmetrical portions 126, 128 of loading surface 124 defined by the first working element 72 allows the entire loading surface 124 to follow the shape of the loaded area 84 of the piece of lumber surface when the latter moves past the location of the deflecting unit 52. It can be seen from FIG. 5 that the central transverse portion of surface 124 defined between symmetrical portions 126, 128 extends in parallel relationship with axis 30' to prevent any significant deformation of the piece of lumber 24 at loaded area 84 thereof. The first displacement mechanism 98 is further provided with a first position sensor including a first limit switch 138 as part of a switch block 140 fit into first bottom mounting plate 62, which limit switch 138 has a protruding contact-activating element secured to a first front mounting flange 142 which is in turn secured to the bearing end 102 of first double member 100, in such a manner that the first limit switch 138 is capable of generating a first control signal whenever the first working element 72 departs from the first static position as shown in FIG. 5 by a first predetermined overload threshold as a result of significant departure of the piece of lumber 24 from the conveying position on rails 78, 78' shown in FIG. 2 as will be later explained in more detail. It can be seen from FIG. 5 that the first working element 90 defines a loading surface 124 extending substantially parallel to the conveying path as indicated by axis 76 in FIG. 2 when disposed in the second static position as indicated by axis 92, 92' in FIGS. 2 and 3B, respectively. It can be also appreciated from FIG. 5 in view of FIGS. 3A and 3B that first and second surface loading portions 126', 128' defined by the second working element 90 also extend toward respective spaced apart portions 77, 77' of piece of lumber 24 transversely to the conveying direction according to a symmetrical angle $\alpha_l$ defined by axis 136' on FIG. 5 which extends from surface loading portion 128' and with respect to an axis 30" parallel to testing axis 30 shown in FIG. 3B, which symmetrical angle a, being substantially proportional to the second deflection magnitude $d_l$ along axis 86 of FIGS. 3A and 3B. For a given transverse span between rails 80, 80' as shown in FIG. 1, which is typically of about 6 feet for a 10-feet piece of lumber, symmetrical angle $\alpha_l$ will have a value of about 2°, to allow the entire loading surface 124 defined by second working element 90 to follow the shape of the loaded area 94 of the piece of lumber surface when the latter moves past the location of second deflecting unit 54. It can be seen from FIG. 5 that the central transverse portion defined between symmetrical portions 126', 128' is shaped in parallel relationship with axis 30"' to prevent any significant deformation of the piece of lumber 24 at loaded area 94 thereof.

Turning back to FIG. 5, the second deflecting unit 54 further includes a second displaceable mechanism 98' for holding the second working element 90, which displaceable mechanism 95' is preferably identical to the first double displaceable mechanism 98 as described above, and therefore similarly includes pivot member pairs 67, 68, 69 and third double-member 100' having bearing end 102' and working end 104' secured to a further pivot member pair 106' as better shown in FIG. 2, a second actuator 108' having a linearly displaceable piston 110' at the end of which is attached a second end coupling element 112' as better shown in FIG. 5, a fourth double member 116' having bearing and working ends 122' and 128'. Similarly, the second working element 90 has its rear portion 115 pivotally secured to the pivot member pair 106' through pivot member pair 106' and has a front portion 121 pivotally secured to working end 118' as part of the forth double member 116'. In a same way, the second displaceable mechanism 98' is selectively controllable to move the second working element 90 between the second static position indicated by axis 92 in FIG. 2 and a retracted position as shown in FIG. 6 wherein the second working 90 is brought away from the conveying path to prevent obstruction thereof. The second displaceable mechanism 98' is provided with a second position sensor in the form of a second limit switch 144 as part of a switch block 146 fitted into second bottom mounting plate 62', which limit switch 144 has a contact-activating element secured to a second mounting flange 142' which is in turn secured to bearing end 102' of the third double member 100' provided on second displaceable mechanism 98'. As will be later explained in more detail, the second limit switch 144 generates a second control signal whenever the second working element 90 departs from the second static position as indicated by axis 92 and 92' in FIGS. 2 and 3B respectively, by a second predetermined overload threshold as a result of the departure of piece of lumber 24 from its normal conveying position onto the rails 80, 80' as shown in FIGS. 1 and 2.

Turning again to FIG. 5, the first displaceable mechanism 98 is provided with a third position sensor in the form of a third limit switch 148 which cooperates with double-switch block 140 to generate a third control signal whenever the first working element 72 substantially departs from the first static position indicated by axis 74, 74' in FIGS. 2 and 3B respectively, by a third predetermined overload threshold greater than the above-mentioned first overload threshold as a result of the departure of the piece of lumber 24 from its normal conveying position on rails 78, 78' as will be later explained in more detail. Also secured to front mounting flange 142 is a stopper 139 adjusted to prevent any damage that could be made to either switch 138 or 148 in case where the first displaceable mechanism 98 is over-extended when reaching the limit stroke of piston 110. A further stopper (not shown) is mounted on the flange 142' to prevent any damage that could be made to switch 144. Each working element 72, 90 preferably defines an article feed guiding surface 150 generally extending toward the loading surface 124 according to an appropriated acute angle $\beta_1$, $\beta_2$ with respect to the conveying path represented by axis 76', 76" in FIG. 5 which angles $\beta_1$, $\beta_2$ have typical values of about 15° and 7°, respectively. It can also be seen from FIG. 5 that the second working member 90 is provided with a symmetrical article output guiding surface 152 presenting an angle $\theta$ with respect to conveying path represented by axis 76" the value of which angle $\theta$ being typically set to about 15°. It can be appreciated from FIG. 5 that no such output guiding portion is provided on the first working element in the example shown since first and deflecting units 52, 54 are located so as to provide and uninterrupted testing sequence to obtain first and second deflection magnitudes $d_s$ and $d_l$ as will be later explained in more detail.

Figure 7:
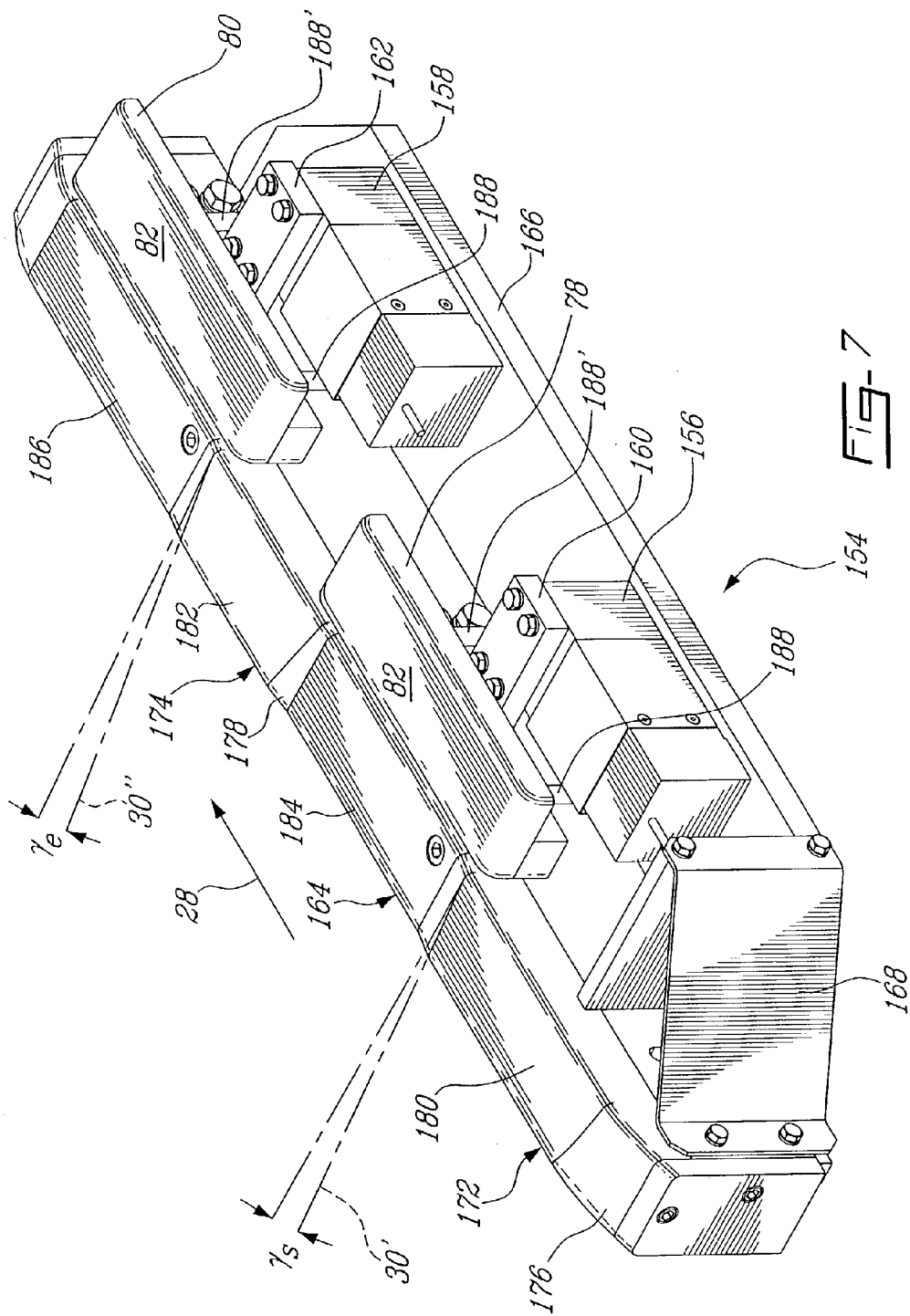
FIG. 7 is a perspective view of first (right) one of the pair of rails as part of the article bearing unit and corresponding load measuring subunit according to the first embodiment.

Turning back to FIG. 2, the apparatus 20 further includes a load measuring unit formed by right and left side subunits generally designated at 154, 154' in FIG. 1. Load measuring subunits 154, 154' are capable of generating signals indicative of respective magnitudes of first and second thrusts as applied by first and second deflecting units 52, 54 as will be later explained in more detail. Since subunits 154, 154' conveniently include the same components in symmetrical configurations, the description below will be limited to the right side subunit 154, which description can be also applicable to subunit 154' using corresponding reference numerals as shown in FIG. 7. It can be further seen from FIG. 5 in view of FIG. 2 that the dimension of loading surface 124 parallel to the conveying direction along the conveying path indicated at 76 in FIG. 2 and 76', 76" in FIG. 5, is larger than the transverse dimension of the piece of lumber 24 under test at the intermediary portion thereof wherein loaded areas 84 and 94 are located as shown in FIG. 3A, so that each loaded area 84, 94 substantially extends over the whole transverse dimension of the piece of lumber 24 while the thrust magnitude indicated signals are generated by the load measuring unit.

Figure 4:
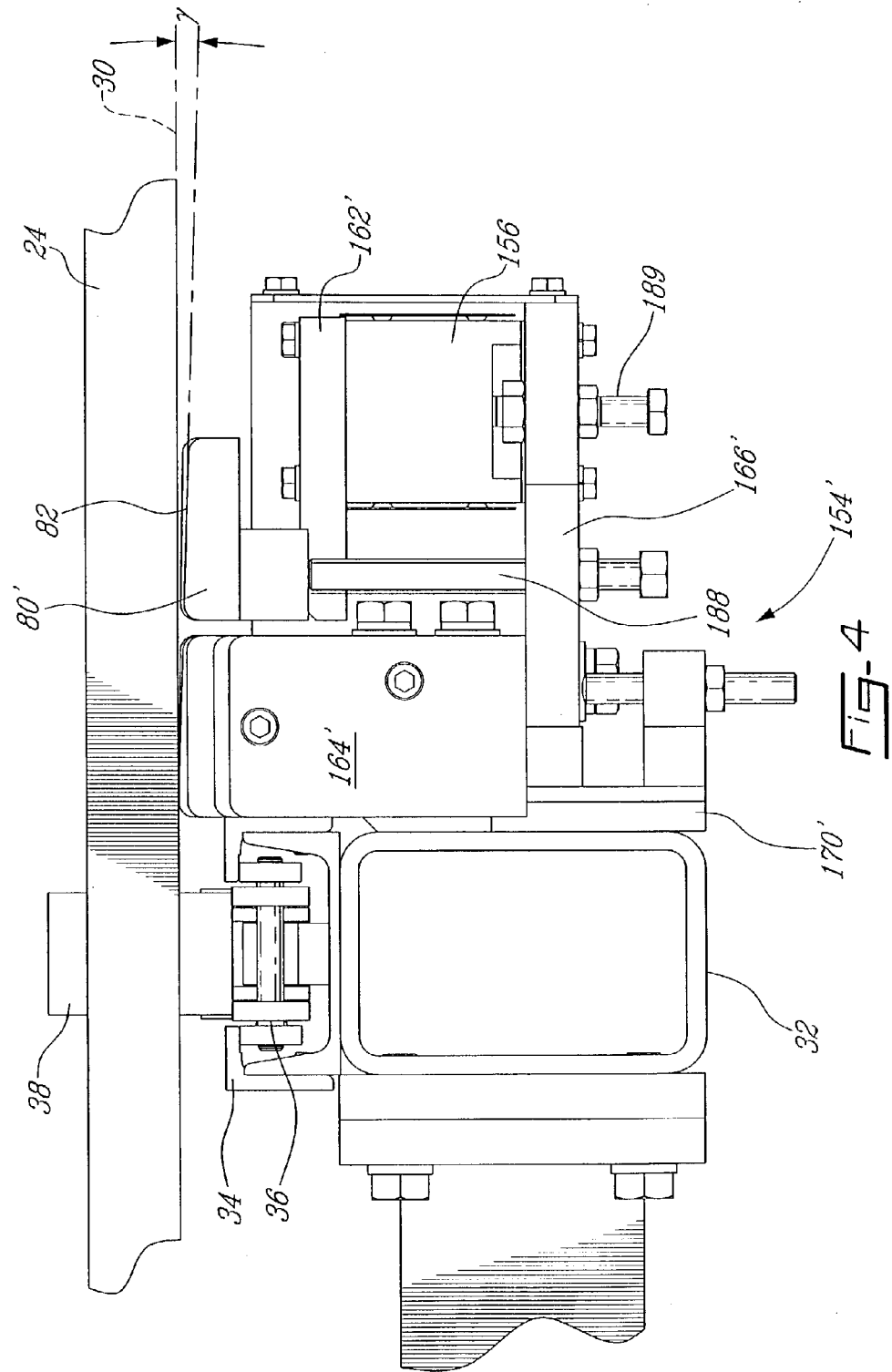
FIG. 4 is a detailed view of the first embodiment of FIG. 3A, showing (left) one of load measuring subunits provided on the apparatus.

Turning to FIG. 7 in view of FIG. 2, the load measuring subunit 154 preferably makes use of two load sensors using load cells 156, 158, such as 250 kg rated load cells model no.125-250KG-I5-IP65 from Tedea-Huntleigh Inc. (Canoga Park, Calif., U.S.A.) used in combination with conditioning amplifying filter unit model no. 460-115 from the same supplier, having load coupling members 160, 162 receiving corresponding rails 78, 80 in rigid connection thereto. The load subunit 154 further includes an elongate guide member 164 to which is attached a load cell supporting plate 166 using flanged plate 168, which guide member 164 is in turn rigidly secured to conveyor frame beam 32" shown in FIG. 1, in a same way as guide member 164' is secured to frame beam 32 using back wall 170' as shown in FIG. 4. Turning back to FIG. 7 in view of FIG. 1, it can be seen that each elongate guide member 164, 164' is disposed relative to the article conveying path represented by axis 76', 76" in FIG. 5 in the conveying direction indicated at 28 in FIG. 1, to set the piece of lumber 24 on the load bearing surface 82 of rails 78, 78' and 80 and 80' as the piece of lumber 24 moves through the apparatus 20. The elongate guide members 164, 164' are disposed in a parallel spaced relationship and longitudinally extend in the conveying direction 28 as shown in FIG. 1. As better shown in FIG. 4, each load bearing surface 82 defined by first and second pairs of rails 78, 78' and 80, 80' disposed at first and second spaced apart location along the conveying path in conveying direction 28, further extends toward the intermediary portion of the piece of lumber 24 transversely to the conveying direction according to angles $\gamma_s$, $\gamma_l$ with respect to the testing axis 30 which are respectively proportional to the first deflection magnitude $d_s$ for rails 78, 78' and to the second deflection magnitude $d_l$ for rails 80, 80'. Such angular configuration allows each load bearing surface 82 to best follow the shape of loaded areas 84, 94 as shown in FIG. 3A when the piece of lumber 24 moves past the location of first and second deflecting units 52, 54 along the conveying path. The guide member 164 has first and second transfer sections 172, 174 disposed in a spaced relationship in the conveying direction indicated by arrow 28 to sequentially set a piece of lumber 24 on respective load bearing surfaces 82 of first and second rails 78, 80 when the piece of lumber respectively moves past the locations of first and second deflecting units 52 and 54 shown in FIG. 1. As shown in FIG. 7, the first transfer section 172 has a receiving portion 176 disposed upstream article setting portions 180. The setting portion 180 of first transfer section 172 extends toward the intermediary portion of piece of lumber 24 transversely to the conveying direction 28 according to angle $\gamma_s$ with respect to axis 30' parallel to testing axis 30 of FIG. 3B, which angle $\gamma_s$ is substantially proportional to first deflection magnitude $d_s$, corresponding typically to an angular value of about 1°. In a similar way, the setting portion 182 of second transfer section 174 adjacent to transition 178, extends toward the intermediary portion of the piece of lumber transversely to conveying direction 28 according to the same angle $\gamma_s$ value, to provide stability to the piece of lumber while it leaves the support surface 82 of first rail 78. The same article setting portion 182 of second transfer section 174 further extends toward intermediary portion of the piece of lumber transversely to conveying direction 28 according to an angle $\gamma_l$ with respect to axis 30" parallel to testing axis 30 of FIG. 3B, which angle $\gamma_l$ progressively reach a value substantially proportional to second deflection magnitude $d_l$, corresponding typically to an angular value of about 2°, to provide a progressive, smooth transfer of the tested piece of lumber between respective surfaces 82 of first and second rails 78, 80. It can be seen from FIG. 7 that intermediary portions 184, 186 of guide member 164 which are transversely aligned with the support surfaces 82 of rails 78, 80 respectively, each extends at a lower level with respect to support surfaces 82 to prevent any mechanical interference with the piece of lumber moving past rails 78, 80. It can also be seen that the load measuring units 154, 154' are provided with two sets of stop elements 188, 188' associated with each rail 78, 80, as well as with a further central stopper 189 aligned with the loading axis of each load cell as shown in FIG. 4, to prevent damage of load cells 156, 158 whenever overload is applied thereto.

Turning back to FIG. 2, the apparatus further includes a data processing device in the form of a computer 190 receiving through lines 192, 192' and 194, 194' the applied thrust magnitude indicative signals generated by pairs of load cells 156 and 158 as described before. The computer 190 is provided with suitable logic and analog input signals conditioning circuitry (not shown) such as a low-frequency filter, as well known in the art. Connected to computer 190 are a terminal display 196 and a data entry device such as keyboard 198 as part of a control panel for use by an operator. The computer 190 may be any suitable industrial microcomputer such as supplied by Advantech Inc. (Cincinnati, Ohio, U.S.A.) making use of Pentium III—800 MHz CPU provided with a suitable digital conversion board such as model No. 3107 from Keithley Instruments Inc. (Cleveland, Ohio, U.S.A.) having 16-bits resolution in analog mode with 16 analog input ports with four groups of 8 digital input/output ports. In the preferred implementation, 4 analog inputs ports in differential mode with two groups of 8 digital inputs with a single group of 8 digital outputs are used. Also operatively connected to the computer 190 is a controller such as programmable logic controller (PLC) 200 connected through analog control lines 202, 204 to a pair of pneumatic servo regulators 210, 212, such as model number ITV3050-31N1L4 from SMC Corp. (Indianapolis, Ind.), which regulators 210, 212 have respective output pneumatic lines 203, 205 operatively connected to a pair of reversing valves 207, 209 whose output are connected to respective air inputs of first and second pneumatic actuator 108, 108' using air lines (not shown). The servo regulators 210, 212 are fed with pressurized air source (not shown) in a known manner, to set air pressure delivered by valves 207, 209 at appropriate levels according to the analog signals received from PLC 200, as will be later explained in more detail. The PLC 200 is connected to reversing valves 207, 209 via further control lines 202', 204' to command either lifting or extension of deflecting units 52, 54. The controller 200 has a further control line 214 connected to a marker or printing device 211 that is used for applying a mark onto a tested piece of lumber as will be explained later in more detail. The apparatus 20 further includes a first presence sensor associated with the first deflecting unit 52, which device is preferably formed of three photo-sensitive cells (PSC), 216, 217, 218 such as Allen Bradley model No. 42GRU-9200-QD1 from Rockwell Automation (Milwaukee, Wis.) respectively aligned with light-reflective elements 220, 221, 222 such as Allen Bradley model No. 92-39 form the same supplier. In a well known manner, adjustably secured to a holding track 219 fixed to the conveyer frame central beam 32' as shown in FIG. 1, PSCs 216, 217, 218 are disposed at the first deflecting unit location along article conveying path 76 so as to be capable of generating control signals fed to the computer 190 through control lines 223, 224, 225 whenever the piece of lumber 24 under test moves past the location of the first deflecting unit 52. Similarly, a second presence sensor associated with a second deflecting unit 54 in the form of three further PCS's 226, 227, 228 respectively aligned with light-reflective elements 235, 237, 239 adjustably secured to holding track 219, is disposed at the location of the second deflecting unit 54 along article conveying path 76 for generating control signals fed to computer 190 via control lines 229, 230, 231, whenever the piece of lumber 24 moves past the second location. It can be seen from FIG. 2 that the first limit switch 138 uses a corresponding control line 232 to send a first overload position indicating signal to the computer 190. Similarly, the second limit switch 144 uses a corresponding control line 233 to send a second overload position indicative control signal to computer 190. In a similar manner, the third limit switch 148 as shown in FIG. 5 uses a further control line 234 to send a corresponding third overload position indicative signal to the PLC 200, as will be explained later in more detail. The stiffness apparatus 20 preferably includes an obstacle presence sensor 236 provided with a contact-activation rod 238 disposed upstream from the location of the first deflecting unit 52 to be capable of detecting any coming article to be tested that significantly departs from the normal, predetermined position relative to catch blocks 38 used by the conveyer system 22 while moving in a conveying direction along conveying path 76. The extremity of rod 38 is positioned in such a manner than any misplaced article such as edge-standing or additional piece of lumber driven by a same catch block will deviate the contact activation rod to cause a fourth control signal to be fed to the PLC 200 through line 240. The rotary encoder 40 uses a corresponding line 242 fed to the PLC 200 with a displacement indicative signal as will be later explained in more detail. Conveniently, the computer 190 may be linked to production control equipment provided in the processing line such as master PLC 244, sending pacer and running conveyer signal through lines 245, 250 in a known manner. A main task of the computer 190 is to generate an estimation of the stiffness of the article tested, which estimation is preferably expressed at the modulus of elasticity E of the article, derived from applied thrust magnitudes as measured by the load cells of the load measuring unit and from the differential deflection value which is mainly dependant from the initial, static relative positions of first and second working elements 72, 90, but also to a significant extent to the structural deformation occurring when thrusts are applied by deflecting units 52 and 54 as will be later explained in more detail. The program stored in the computer 190 makes a calculation of the modulus of elasticity E of each tested piece, considering its specific dimensions, applied load measurement values and corresponding deflection values, according to an approach which is insensitive to the natural curvature exhibited by each piece tested. According to the present example, the software has been programmed using Labview™ (version 6) graphic programming tool available from National Instruments Corp. (Austin, Tex.) which runs within Microsoft Windows™ NT4 environment. Conveniently, an executable version off the program is loaded in the computer, along with a parameter setup file that contains all program initialization parameter values that can edited at will by the operator. The raw Young modulus values so obtained are preferably corrected using predetermined dynamic and static correction factors, to convert the raw data into usable data that can be compared to standard modulus of elasticity data obtained with a reference static testing bench. The corrected resulting values are then compared to a table of predetermined reference values defining ranges corresponding to a number of MSR grades or classes to assign a specific one of these classes to each tested piece of lumber. Preferably, the resulting classification information is communicated through one of output lines 246, 247, 248 associated with three different color codes corresponding to pre-selected MSR classes, causing PLC 200 to control the printing device 211 accordingly, the latter being provided with three corresponding printing nozzles in a fluid communication with tanks containing inks of different colors. The computer program is also adapted to monitor the various functions of the apparatus 20 through the various sensors, to communicate via computer display 92 function monitoring data to an operator, or to a master PLC 244 as part of the production line. The main programs stored in computer 190 provides a plurality of screens and sub-screen which allow an operator to assign desired values for the operating parameters, to have access to values indicators giving in real-time the classification results in term of assigned MSR grade for each tested piece, to receive apparatus functions status information along with alarm messages for directing the operator's attention to specific anomalies that may occur when the apparatus is working.

Prior to the operation of the apparatus 20, first and second static positions of first and second working elements 72 and 90 are set using the adjustment mechanism 123 provided on each actuator 108, 108' as described before with reference to FIG. 5, so as to obtain a resulting differential deflection value Δd preferably involving a substantially linear portion of the curve representing bending stress behavior of the article under test. Typically, on the basis of equation (1) described before, the first working element 72 is positioned so as to have $d_s$=0.65 cm and to have $d_f$=1.3 cm to obtain a resulting value for Δd close to a nominal value $Δd_n$=0.65 cm, after applying correction factors as will be described later in detail.

In operation, a first incoming piece of lumber 24 adequately positioned against an adjacent transverse series of catch blocks 38 as driven by chain 36 of conveyor system 32 passes under obstacle presence sensor 236 which is not activated since the piece of lumber 24 is in a proper conveying position as shown FIG. 2. Then, the incoming piece of lumber 24 reaches the guiding surface 150 provided on the first working element 72 while contacting the article receiving portion 176 of each guide member 164 as shown in FIG. 7, intersecting the detecting beam of the first photo-sensitive cell 216 which is caused to generate a "on" signal transmitted to the computer 190, indicating that a piece of lumber 24 will shortly enter the thrust applying zone defined by the first working element 72. Then the leading side edge of the lumber piece 24 reaches the article setting portion 180 of first working element 72 to guide and progressively set the piece of lumber 24 under test onto the load bearing surface 82 of first pair of rails 78, 78' in sliding movement relative thereto. Then, the piece of lumber 24 intersects the detecting beam of the second photo-sensitive cell 217 causing the generation of a control signal sent to the computer 190 through line 224 for triggering data acquisition of load measurement signals from the first pair of load cells 156 transmitted to the computer 190 through lines 192, 192'. It can be seen from FIG. 2 that the second photo-sensitive cell 217 and its associated reflective device 221 are aligned in a position relative to the first pair of rails 78, 78' in the direction of the conveying path 76 so as to ensure that the tested piece of lumber 24 is completely in contact with the load bearing surface 82 and the loading surface 124 of the first working element 72, in such a manner that the load cells 156 generates substantially stable signals. While the computer 190 performs load measurement data acquisition at a predetermined sampling frequency, it also reads the status of binary signals coming from PSCs 216, 217, 218 as well as from limit switches 138, 138' and 144 for storing in computer memory. The computer continues to read and store analog and binary signals until the piece of lumber 24 intersects the detecting beam of the third photo-sensitive cell 218 or after a preset duration stored in the computer which is determined according to a maximum duration required for data acquisition. It is pointed out that the effective load measuring zone defined by the positions of second and third photo-sensitive cells 217, 218 must extend over a sufficient length to allow reliable data acquisition, considering the acquisition sampling rate, transverse dimension of piece of lumber 24 as well as conveying speed of the conveyor system 32. Furthermore, the load-measuring zone preferably extends over a distance corresponding to two conveyor chain links in such a manner to substantially cancel load measurement fluctuation due to the use of a chain to drive the catch blocks 38. Then, while leaving the load bearing surface 82 of first pair of rails 78, 78' the piece of lumber 24 reaches the article receiving portion 178 of the second transfer section 174 as part of guide member 164 so as to progressively enter within the thrust applying and load measuring zone defined by the second working element 90 and corresponding pair or rails 80, 80'. Then, the piece of lumber 24 intersects the detecting beam of photo-sensitive cell 226 as part of the second presence sensor, causing the generation of a control signal sent to the computer 190 through line 229 for triggering data acquisition of load measurement signals from the second pair of load cells 158 transmitted to the computer 190 through lines 194, 194'. It can be seen from FIG. 2 that the photo-sensitive cell 226 and its associated reflective device 235 are aligned in a position relative to the second pair of rails 80, 80' in the direction of the conveying path 76 so as to ensure that the tested piece of lumber 24 is completely in contact with the load bearing surface 82 and the loading surface 124 of the second working element 72, in such a manner that the load cells 158 generates substantially stable signals. While the computer performs load measurement data acquisition at a predetermined sampling frequency, it also reads the status of binary signals coming from PSCs 226, 227, 228 as well as from displacement encoder 40, limit switches 138, 148 and 144 for storing in computer memory. The computer continues to read and store analog and binary signals until the piece of lumber 24 intersects the detecting beam of the photo-sensitive cell 227 or after a preset period of time stored in the computer which is determined according to a normal period of time required for data acquisition. Here again, the effective load measuring zone defined by the positions of photo-sensitive cells 226, 227 must extend over a sufficient length to allow reliable data acquisition. The data acquisition being completed, the computer program automatically starts calculation of the modulus of elasticity value associated with each tested piece of lumber 24 according to a process that will be now described below. First, a mean load measurement value is calculated for each load cell as follows:

$$RawLoad[i] = \left(\frac{\sum_{j=1}^{n} Load[i][j]}{n}\right) * K_{kg} \quad (2)$$

with: Load = Voltage − 0.5 wherein:

i is a cell identification indicia, with i=1,2 indicating the load cells 156 coupled to the first pair of rails 78, 78' and associated with the first deflecting unit 52, while i=3,4 indicating the load cells 158 coupled to the second pair of rails 80, 80' and associated with the second deflecting unit 54;

n is the number of load measurement data samples read;

$K_{kg}$ is a predetermined factor (kg/Δvolt) for converting the measurement in kg unit;

Load is a corrected load measurement voltage generated by each load cell 156 as corrected by a predetermined offset value characterizing the load cell when unloaded.

Then, the obtained value for RawLoad[i] is preferably corrected using a predetermined tare correction value to compensate for the output level drift to which each load cell is subjected with time, the value of which can be measured when no load is applied to the load cell. The offset value can be established through an initial or periodic manual calibration procedure. The computer calculates a corrected or net load measurement value from the estimated tare value for each load cell of indicia i as follows:

NetLoad[i]=RawLoad[i]+Tare[i]     (3)

Then, the computer program calculates the load applied by each deflecting unit 52, 54 as well as a total applied load value as follows:

NetLoad$D_s$=NetLoad$_1$+NetLoad$_2$     (4)

NetLoad$D_l$=NetLoad$_3$+NetLoad$_4$     (5)

Load$_T$=NetLoad$D_s$+NetLoad$D_l$     (6)

wherein:

NetLoad$D_s$ is the net load value applied by the first deflecting unit 52 imparting the smaller deflection magnitude $d_s$; and NetLoad$D_l$ is the net load value applied by the second deflecting unit 54 imparting the larger deflection magnitude $d_l$; and Load$_T$ is the total applied load value.

On the basis of the above calculations, the computer preferably applies a correction to the nominal deflection values as set prior to the operation of the apparatus, to compensate the inherent deformation to which the whole structural components of the apparatus are subjected, such as load cells flexion, flexion of overhead beams 48, twist induced by the second deflecting unit 54 imparting the larger deflection $d_l$, and friction with the load bearing surfaces 82 of each rail 78, 78', 80, 80' while the tested articles are sliding thereon. It is pointed out that some marginal factors such as twist induced by the second deflecting unit 54 imparting the smaller deflection $d_s$ may be ignored as having non-significant effect on the result. The correction is made on the basis of estimated deflection error values associated with the smaller and larger deflection values $d_s$, $d_l$ as calculated as follows:

$$ErD_s = \left(\frac{NetLoadD_s}{2} * K_{Cell}\right) + (Load_T * KS) + \quad (7)$$
$$(NetLoadD_l * KTwist_{ls}) + (Load_T * KFric_s)$$

$$ErD_l = \left(\frac{NetLoadD_l}{2} * K_{Cell}\right) + (Load_T * KS) + \quad (8)$$
$$(NetLoadD_l * KTwist_{ll}) + (Load_T * KFric_l)$$

wherein:

$K_{Cell}$ is a predetermined constant factor (N*m) representing stiffness characterizing the load cells and corresponding load measuring subunits;

KS is a predetermined constant factor (N*m) representing stiffness characterizing the structural components of the frame including overhead beams 48 and conveyer frame beams 32, 32";

$KTwist_{ls}$ is a predetermined constant factor (N*m) representing cross-twist induced by the thrust applied by the second deflecting unit 54 to the first working element 72;

$KTwist_{ll}$ is a predetermined constant factor (N*m) representing twist induced by the thrust applied by the second deflecting unit 54 to the second working element 90;

$KFric_s$ is a predetermined constant factor (N*m) representing twist induced by the friction between the loaded surface of the tested article and the loading surfaces of first and second working elements 72,90, having a corresponding influence to the smaller deflection value;

$KFric_l$ is a predetermined constant factor representing twist induced the friction between the loaded surface of the tested article and the loading surfaces of first and second working elements 72,90 having a corresponding influence to the larger deflection value;

Then, on the basis of the above error estimates, a corrected differential value is derived from the nominal deflection $\Delta d_n$ value as follows:

$\Delta d = \Delta d_n - ErD_l + ErD_s$     (9)

Then, the computer proceeds with calculation of a raw modulus of elasticity for the tested article according to the following relations:

$$RawE = \frac{\Delta Load \times S^3}{48 \times I \times \Delta d} \text{ with} \quad (10)$$

$\Delta Load = NetLoadD_l - NetLoadD_s$     (11)

$$I = \frac{W \times T}{12} \quad (12)$$

wherein:

S is the span (in cm) extending between the load bearing surfaces 82 of each pair of rails 78, 78' and 80, 80';

I is the inertia modulus value for a tested piece having rectangular section;

W is the transverse width dimension (in cm) of the tested piece; and

T is the thickness dimension (in cm) of the tested piece.

From the raw modulus of elasticity obtained, the computer program then applies dynamic and static edge corrections based on the relation existing between dynamic and static edge bench testing results, characterizing the mechanical stress behavior of the specific type of article being tested (i.e. 2×3, 2×4 pieces of lumber), for obtaining an modulus of elasticity estimation that could be compared to reference data obtained from standard static bench testing. Such relation may be expressed as follows:

$$E = K_{Stat} \times K_{Dyn} \times RawE$$

wherein $K_{Dyn}$ is a factor characterizing the relation between dynamic and main surface-based static testing results;

$K_{Stat}$ is a factor characterizing the relation between main surface-based and edge-based static testing results.

Such relation may be experimentally established by testing first a batch of pieces using a standard edge testing static bench, on the basis of a known Standard such as NLGA SPS-2, SPS-3 as well known in the art, which pieces are classified by comparing the standard edge-based modulus of elasticity values obtained with predetermined ranges defining a group of selected standard MSR classes, for example a group of three selected MSR classes. The same batch of pieces is also tested using a standard bench capable of applying load onto the main surfaces of the lumber pieces, to obtain surface-based modulus of elasticity values that can be associated with the standard edge-based modulus of elasticity values. The same batch of pieces is further tested according to the procedure described above to obtain raw modulus of elasticity RawE values that can be associated with the standard edge-based and main surface-based modulus of elasticity values. Average values associated with each MSR class considered are then computed for the raw modulus of elasticity as well as for associated main surface-based and edge-based modulus of elasticity values. From the resulting average values, the dynamic correction factors as well as static correction factors for each type of article involved (i.e. 2×3, 2×4 pieces) are calculated. The above procedure may be repeated with additional groups of selected MSR classes so as to establish the correction factors for a complete set of MSR classes, as given in the exemplary table shown in the displayed screen of FIG. 12. To perform calculation of the resulting net modulus of elasticity value E for a given raw modulus of elasticity RawE value, the computer relies on such table to select the more appropriate values of dynamic and static correction factors, which can be conveniently factor values associated with the closest AverageE value given in the table. The computer program then compares the modulus of elasticity E value as estimated for each tested article with predetermined reference ranges data defining the set of standard MSR classes, for assigning classification data to the tested article accordingly. Such reference ranges data are given in the exemplary table shown in the displayed screen of FIG. 11, wherein the minimum threshold value associated with each MSR class listed has been given the average value as established by the MSR Standard for each MSR class, to ensure that no more than 5% of the classified pieces are over-graded.

Finally, the tested piece of lumber 24 is further advanced through the action the catch blocks 38 past the output guiding surface 152 of second working element 90 while intersecting the detecting beam of the photo-sensitive cell 228 causing the latter to transmit through line 231 a control signal to the PLC 200 indicating that the controller 200 can be set to activate a selected ink nozzle provided on the printing device 210 when the tested piece of lumber 24 passes thereunder. To perform classification, the computer program compares the resulting net E with the threshold value given in the table as displayed on the screen of FIG. 11 which is associated with the MSR class representing the highest quality amongst selected MSR classes. If the current tested piece does not comply with the requirement of such highest quality MSR class, i.e. the resulting E has a lower value compared to the threshold value established for such higher rank class, the computer program makes a further comparison with the threshold value associated with a following MSR class of a lower quality, and the process is continued until the threshold value for the tested piece is found greater than the threshold value of such following MSR class. In cases where the E value for a particular piece is found to be lower than any of threshold values associated with the selected MSR classes, such piece is considered as unclassified and rejected accordingly. After a tested piece has been assigned classification data, the computer software generates a control signal for the PLC 200 via a selected one of lines 246, 247, 248 corresponding to the classification data assigned to the tested piece, which PLC 200 stores such control signal for activating a corresponding valve provided on the printing device 210 which is in fluid communication with a corresponding tank filled with ink of a specific color, following an indication from the computer 190 that a presence detecting signal has been received from PSC 228. It is pointed out that the position of PCS 228 along conveying path 76 as well as the position of the nozzles provided on the printing device 210 are chosen in such a manner that the computer software is capable of completing E calculation before the tested piece reaches the printing device 210, provided the distance between PCS 226 and printing device 210 is within the spacing between two successive transverse series of catch blocks 38 as shown in FIG. 2.

Regarding the tare monitoring function performed by the computer program, the control signal generated by conveyor displacement encoder 40 and first PSC 216 are used by the computer 190 to verify if the apparatus is running while a next piece to be tested is not present in conveying position against a following series of transverse catch blocks 38. If the apparatus is free-running during a period of time exceeding a predetermined duration, the computer software starts a tare estimation subroutine by performing data acquisition of a predetermined number of measurement samples, converts the mean load measurement values in pound unit, and then makes a verification of the tare value for each load cell 78, 78', 80, 80' by comparing the measured value with a predetermined reference value. If the calculated deviation is higher than a predetermined maximal tare error value, the computer program increments a tare error counter, a corresponding tare error signal is sent to the master PLC 244 of the plant, and the classification process may be interrupted depending upon a maximum error as set by the operator is reached. Whenever PSC 216 detects that a next piece is incoming while the tare verification process is in progress, the subroutine is interrupted to return to the normal load measurement mode. The accumulated number of tare errors detected is preferably displayed on the computer screen as shown in FIG. 8.

The computer is also preferably programmed to continuously monitor the status of each of PSCs 216, 217, 218 and 226, 227, 228 used as first and second presence sensors. The program cumulates the number of signal raising fronts generated by each PSC and stores such number in a FIFO dedicated to each PSC. The program calculates the deviation between maximum and minimum numbers of signal transition observed for all PSCs and compares such deviation value with a predetermined maximum deviation threshold to generate an error indicative signal sent to master PLC 244, and the classification process may be interrupted according to criteria set by the operator. The error signal is also used by the computer 190 to display a piece of lumber detection error as shown in the computer screen illustrated in FIG. 8.

The computer 190 is further programmed to perform monitoring of overload detecting limit switch 138, 138' and 144 provided on the apparatus 20. The limit switches 138, 144 are normally in a "on" status indicating that the corresponding working elements 72, 90 are adequately maintained in their respective substantially static positions when the pieces of lumber 24 are traveling through the apparatus. Whenever one of working element 72 or 90 departs from its corresponding static position by a first or second predetermined overload threshold as a result of significant departure of the article from the normal conveying position against catch blocks 38, a corresponding control signal is generated by a corresponding one of limit switches 138, 144 through either lines 232 or 233 depending on which working element has been displaced, causing the computer 190 to cancel the derivation of the modulus of elasticity E for any piece of lumber 24 located within the measuring zone defined by working elements 72 and 90. Conveniently, the first and second threshold may be preset to a same threshold value as desired. The computer program cumulates the number of working element displacements that have occurred when a predetermined number of last tested pieces, ex. 50 pieces, have sequentially passed through the apparatus, by incrementing a counter and storing the event in a FIFO, the FIFO being decremented whenever data is read out from the FIFO. Whenever the displacement rate exceeds a predetermined maximum overload value, such information is displayed in the computer screen illustrated in FIG. 8. When an overload detection error is observed, a control signal is sent to the master PLC, 244, and the classification process may be interrupted depending upon the criteria set by the operator. More specifically, the additional limit switch 148 associated with the first working element 72 generates a control signal transmitted through line 234 that is received by the PLC 200, whenever the working element 72 substantially departs its static position by a predetermined overload threshold greater than the first overload threshold, causing the PLC 200 to generate a control signal addressed to computer 190 through line 143, which PLC 200 in turn commands the first and second displacement mechanism 98, 98' provided on first and second deflecting units 52, 54 to move respective first and second working elements 72, 90 from respective first and second static position shown in FIG. 2 to respective retracted positions as shown in FIG. 6. Furthermore, the computer 190 interrupts the classification process while a corresponding interrupted operation indicative signal is sent to master PLC 244 through line 241. In a similar way, the PLC 200 lifts deflecting units 52, 54 to their respective retracted positions shown in FIG. 6 whenever the PLC 200 receives from upstream presence detector 236 through line 240 a signal indicating that an incoming piece of lumber 24 is not in proper conveying position against adjacent catch blocks 38. While deflecting units 52, 54 may be manually returned to their respective first and second static positions shown in FIG. 2 using a manual selector (not shown) provided on the apparatus, the apparatus preferably uses the displacement indicating signal generated by the encoder 40 and continuously sent to the PLC 200 through line 242, to verify that the transverse series of catch blocks 38 associated with the improperly positioned piece at the origin of the actual or expected overload error condition has been displaced beyond the load applying zone of the second deflecting unit 54, and to command PLC 200 to move back first and second displaceable mechanisms 98, 98' so as to move first and second working elements 72, 90 from their respective retracted positions to respective first and second static positions shown in FIG. 2. The computer 190 also generates a heartbeat binary signal toward the master PLC 244 through line 243. The value of such control binary signal periodically changes every few seconds so that when the master PLC 244 does not detect a signal transition after a predetermined duration, the apparatus 20 is considered as being in an "not ready" mode. Furthermore, the computer 190 may transmit error indicative signals to the master PLC 244 through a further line 249 whenever a problem requiring operator intervention is observed. The computer is also programmed to store in computer memory measurement historical data for a predetermined number of last tested pieces. Typically, for each tested piece, the stored data includes testing date and hour, net load NetLoad[E] value for each load cell, differential load ΔLoad value, resulting modulus of elasticity E and the MSR class assigned to the tested piece. Furthermore, for a given batch of tested pieces, the program stores the current number of pieces for which data has been stored and distribution percentage associated with each MSR class. The load applying force delivered by each pneumatic actuator 108, 108' can be adjusted through corresponding settings made at PLC 200 as commanded by computer 190 through control signals transmitted via line 143, which indicate in the present example whether 2×3 or 2×4 pieces of lumber are being tested. PLC 200 sends a corresponding pressure level indicative signal to pneumatic servo regulators 210, 212 through control lines 202, 204. Typically, the pressure level applied to the first actuator 108 may vary from about 24600 kg/m$^2$ for a 2×3 piece of lumber, to about 35150 kg/m$^2$ for a 2×4 piece of lumber, while the pressure level applied to second actuator 108' may vary from 31600 kg/m$^2$ for a 2×3 piece of lumber to about 42200 kg/m$^2$ for a 2×4 piece of lumber. A predetermined pressure level is further stored in PLC 200 to send corresponding pressure level control signals whenever valves 207, 209 are activated to cause first and second actuators 108, 108' to lift first and second deflecting units 52, 54 in the respective retracted position. The computer 190 receives from PLC 200 through line 145 a further signal whenever the PLC 200 is manually operated to lift deflecting units 52, 54, as well as an echo running conveyer signal through line 149. A preset pressure level applied to actuators 108, 108' to lift both deflecting units 52, 54 is typically of about 63300 kg/m$^2$. It is pointed out that for security purposes, the computer is also programmed to ensure that deflecting units 52, 54 are never automatically raised in their respective retracted position when the displacement encoder 40 indicates that the conveyor system is not running.

Figure 8:
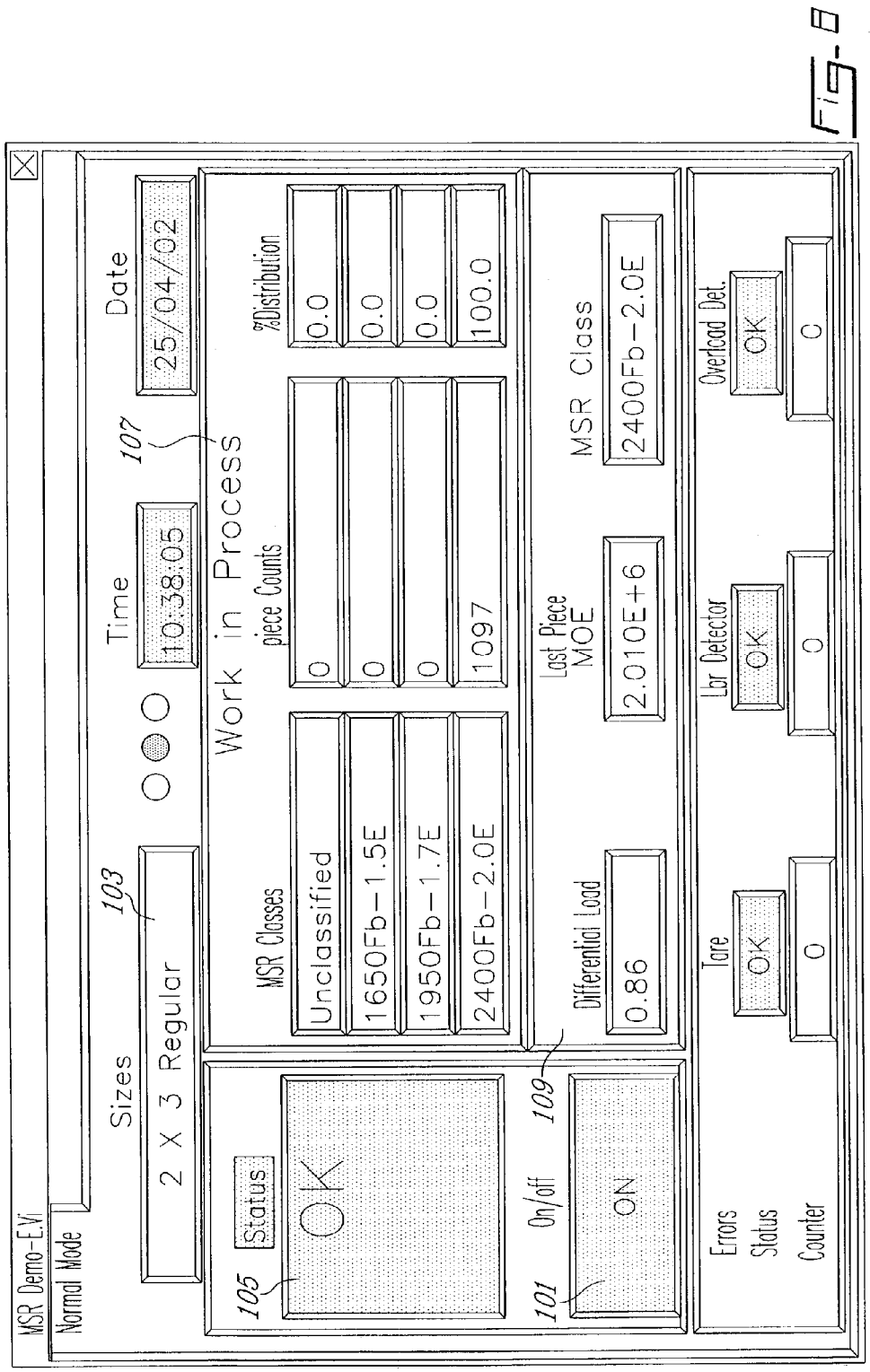
FIG. 8 is a representation of a typical screen generated on the computer display provided on the apparatus while in a normal mode of operation.

Referring now to FIG. 8, a computer screen corresponding to a normal mode of operation of the stiffness testing apparatus according to the invention is illustrated, wherein a "On /Off" button 101 can be activated by the operator through the keyboard 198 provided with computer 190 so as to selectively switch the apparatus between running mode according to which testing are performed on pieces of lumber as conveyed through the apparatus, and a stop mode enabling the operator to set classification parameters, start a tare calibration procedure, or obtain perform dynamic analysis as later explained in detail. As shown in FIG. 8, the window 103 disposed under heading "Sizes" provides an indication of the type of pieces currently being processed. Typically, four types of piece of lumber can be handled, namely 2×3 regular, 2×3 oversized, 2×4 regular and 2×4 oversized. Three light pilots 251 are preferably displayed to indicate that logic input reading, piece classification and logic output management as background running tasks are being performed normally. The "status" window 105 is used to indicate whether the apparatus works normally or to indicate one or more abnormal detected conditions such as lifted deflecting units, tare error, piece of lumber detection error, overload detection error or stop status. To the right of the "status" window 105, a "Work in Process" window 107 displays classification results according to selected MSR classes, wherein quantity of pieces of lumber classified according to each selected MSR class is indicated along with corresponding percentage distribution. A further window 109 displays the testing result obtained for the "last piece" classified, namely differential load measured, the net modulus of elasticity E and the specific MSR class that has been assigned to this last piece. A last window appearing at the bottom of the screen shown in FIG. 8 gives errors status and current counts for tare, piece of lumber detection and overload detection functions as explained before. Whenever the number of abnormal events related to one of these error categories exceeds a corresponding preset threshold, the status indicator switches from "OK" to "alarm" for a preset duration as set by the operator. Furthermore, for some temporary detected events such as limit switch activations that do not justify processing interruption, a corresponding massage can be temporarily displayed as such condition exists.

Figure 9:
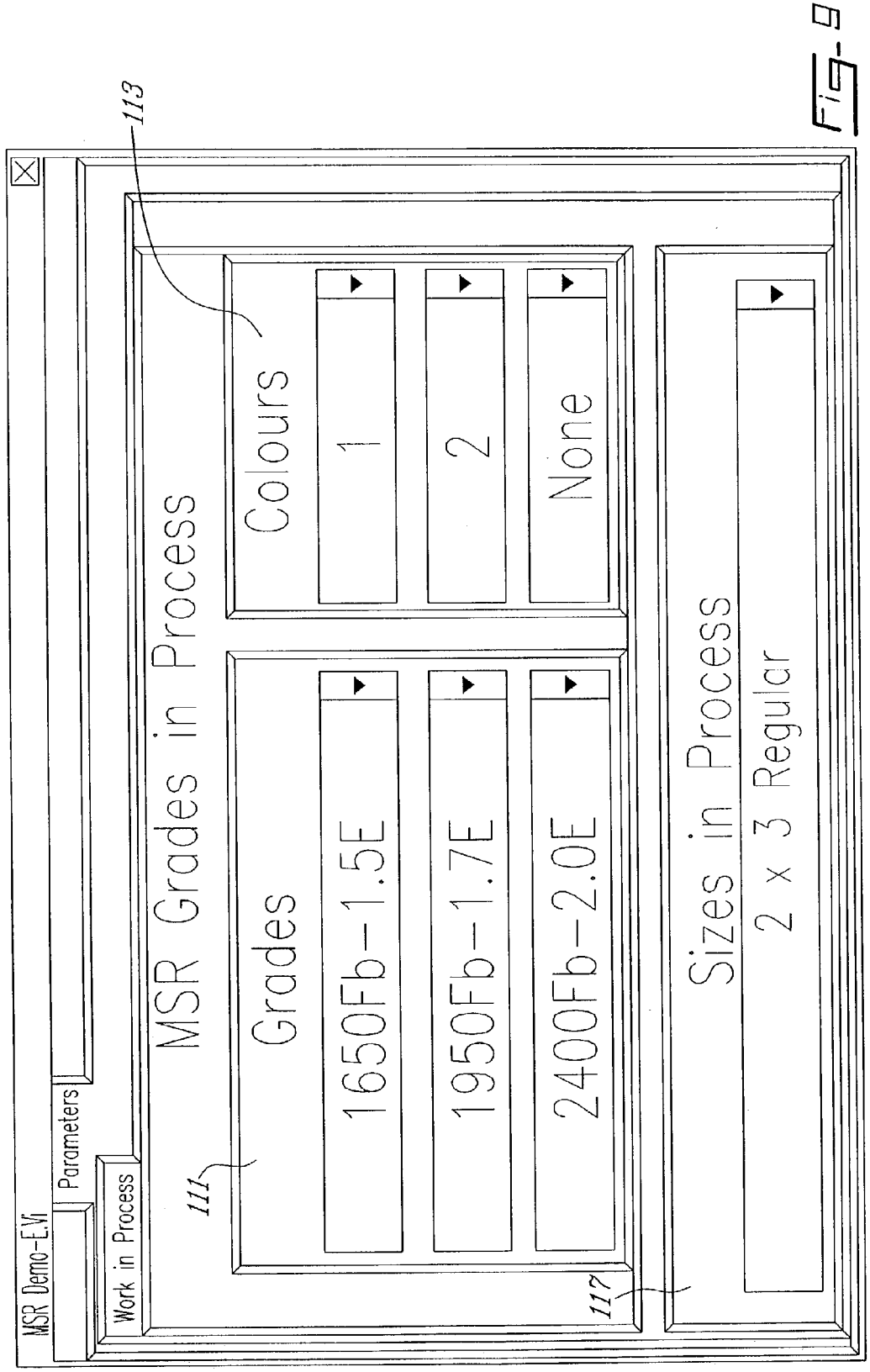
FIG. 9 is a representation of a typical screen displayed while the apparatus is in a parameter-setting mode of operation regarding production-in-progress.

Turning now to FIG. 9, a parameter setting screen as generated by the computer program is illustrated, enabling the operator to assign desired values for a number of parameter categories that can be accessed through corresponding number of sub-screens as illustrated in FIGS. 9 to 12. In FIG. 9, MSR classes or grades under processing can be selected by the operator through window 111 on the basis of the set of MSR classes or grades that has been previously defined such as listed in FIG. 11. In the example shown, up to three selected MSR classes in process can be entered by the operator, each of which being associated with an ink tank that can be selected through window 113 whenever printing is required for these specified MSR classes. At the bottom window 117 of the screen shown in FIG. 9, the specific size for pieces of lumber under processing can be selected by the operator amongst the types listed in FIG. 11.

Figure 10:
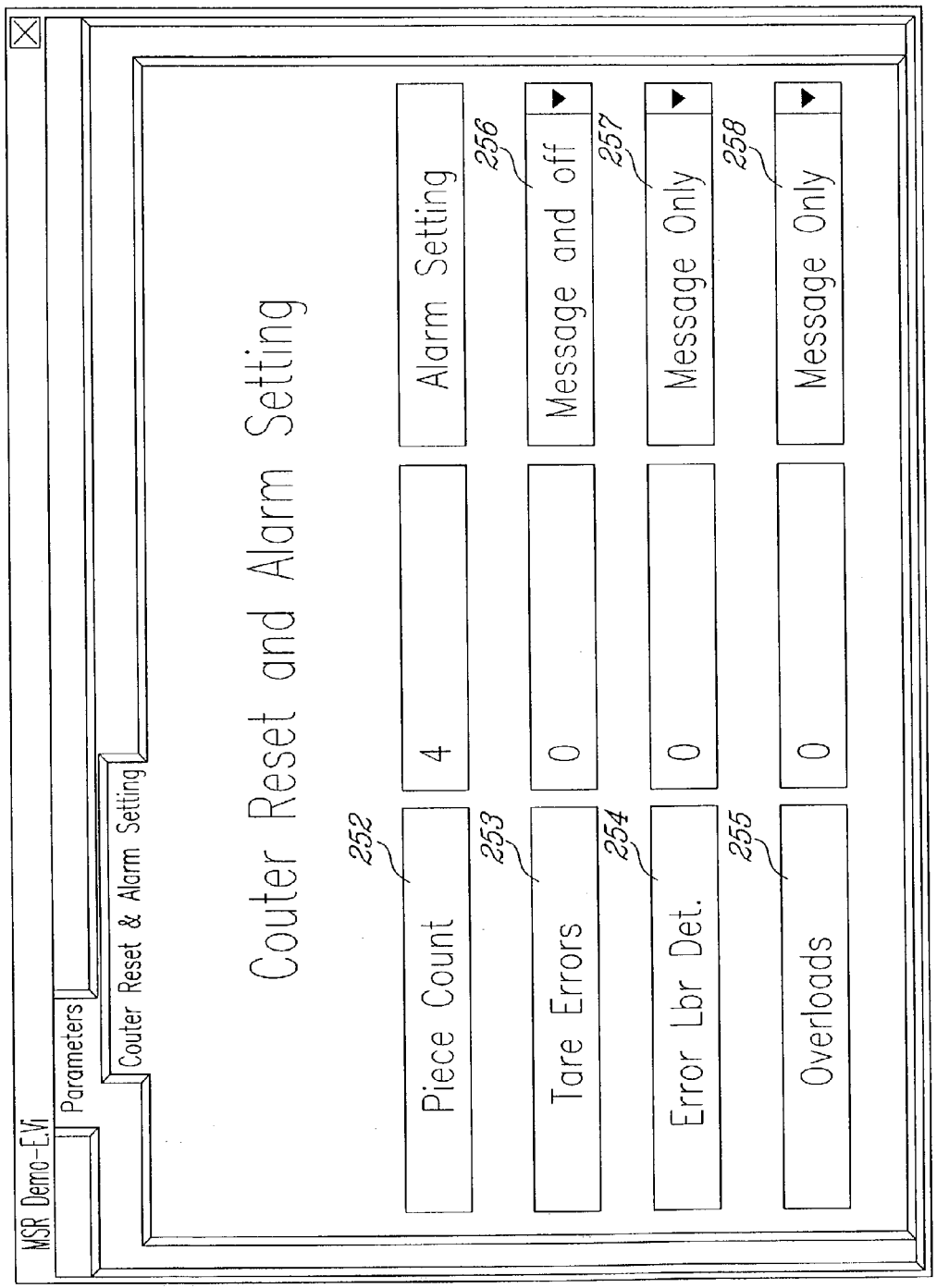
FIG. 10 is a representation of a typical screen displayed while the apparatus is in the parameter-setting mode regarding event counters and alarms.

Turning now to FIG. 10, a further sub-screen allows the operator to reset the various counters as well as modify some operating conditions according to which classification is performed, and to set a desired action to be performed by the computer 190 whenever a particular alarm is activated. A button "Piece Count" at 252 allows the operator to reset to zero the total number of classified pieces as well as corresponding distribution percentage values associated with the specific MSR class displayed on the normal mode screen as shown in FIG. 8. A button "Tare errors" at 253 allows the operator to set the tare error counter to zero. A button "Error Lbr Det." at 254 allows the operator to reset the piece detection error counter to zero. A button "Overloads" at 255 allows the operator to reset the overload error counter to zero. Associated with buttons 253, 254 and 255 are a set of windows 256, 257 and 258 which allow the operator to select an specific action to be taken by the computer program when an alarm is activated, namely: displaying an error message and/or switch to an "off" classification status.

Figure 11:
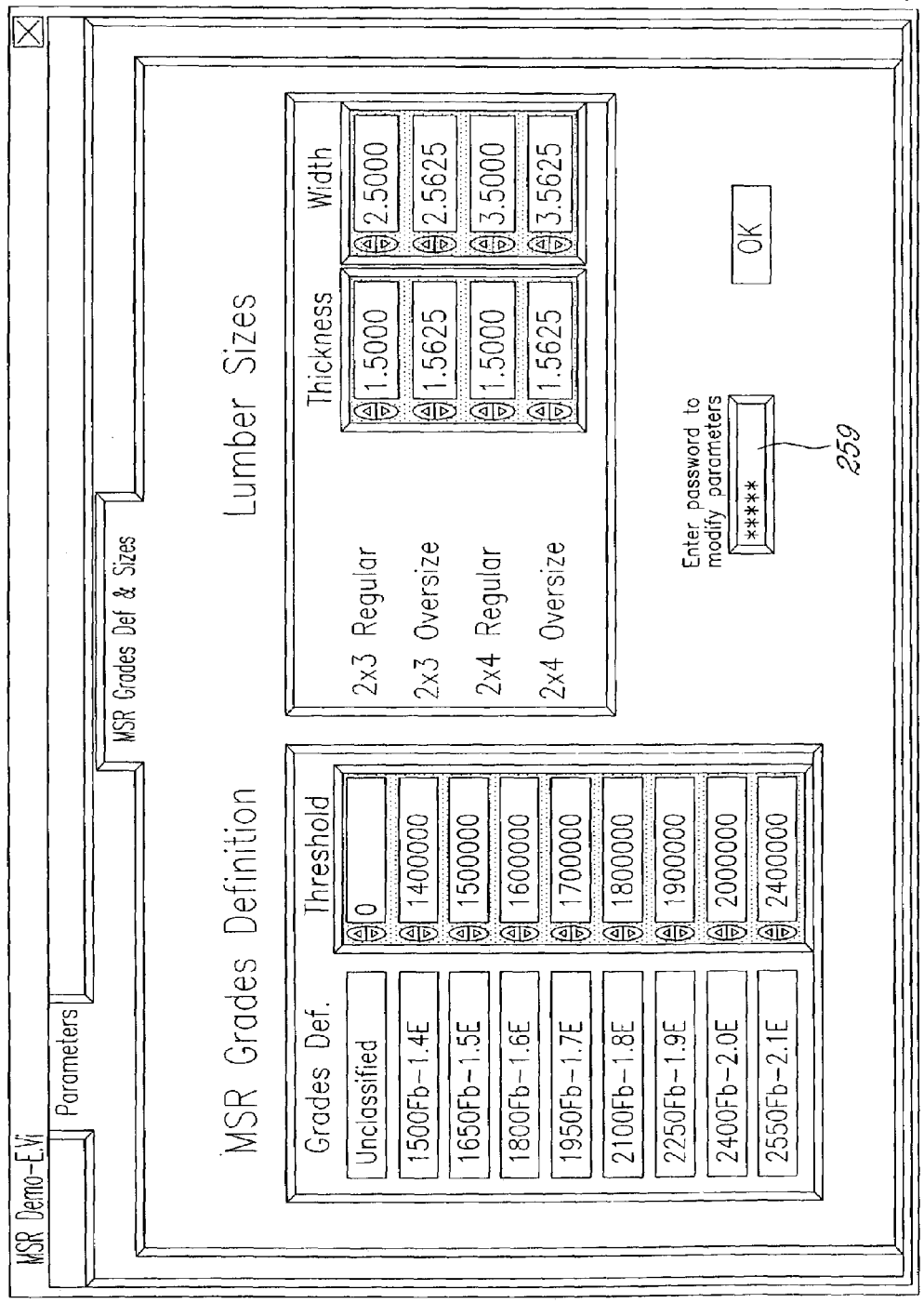
FIG. 11 is a representation of a typical screen displayed while the apparatus is in the parameter-setting mode related to MSR classes and dimensions definition.

Turning now to FIG. 11, the sub-screen shown allows the operator to modify parameters associated with MSR grades and lumber Sizes to be processed, provided the apparatus is set to "off" mode of operation, and an appropriate password is entered via input window 259, to ensure that such basic parameters are set by an authorized person. As explained before, at the left portion of the screen, the definition of pre-established MSR grades with associated minimum threshold values are displayed. At the right portion of the same sub-screen, the various sizes of the predetermined types of pieces are displayed, which sizes are considered in the calculation of the modulus of elasticity E or each piece of lumber as explained before.

Turning now to FIG. 12, a last sub-screen under the heading "Parameters" is shown, which can be used by the operator upon entry of an appropriate password through window 119 to modify correction factors employed by the computer program to calculate the net modulus of elasticity E for each piece, provided the apparatus is set to "off" mode and that an appropriated password is entered. As explained before, a list of predetermined averageE values is used by the computer to determine which ones amongst static correction edge factor $K_{Stat}$ values and dynamic direction factor $K_{Dyn}$ would be the best pair of factor values to use according to the raw modulus of elasticity RawE value obtained for a given piece tested, in a calculation of a net modulus of elasticity E value which can be compared to standard reference classification data.

Figure 13:
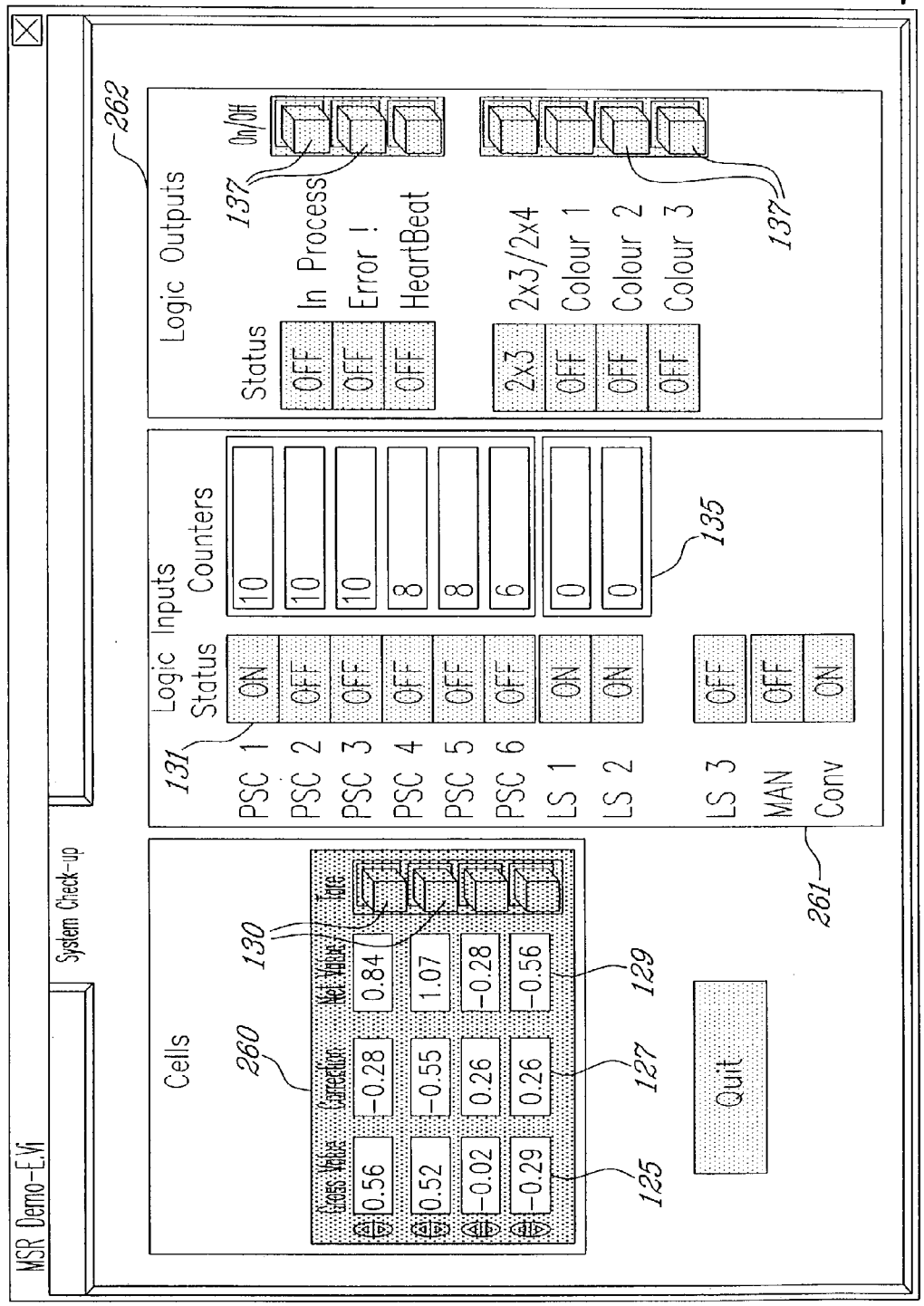
FIG. 13 is a representation of a typical screen displayed while the apparatus is in a system verification mode wherein information about the status of input-output signals involved in the operation of the apparatus is made accessible to the operator.

Referring now to FIG. 13, a further screen associated with heading "System Check-up" allows the operator to visualize the operating status of the main components of the apparatus. At the left of the screen, a window 260 provides an indication of tare level fluctuations that usually occur as the apparatus is running. Through window 260, the operator is allowed to update current tare values set in the apparatus provided the latter is set to "off" mode. To the left of window 260, a first column at 125 gives values of gross tare deviation from zero as measured for each load cell (in pound). A next column 127 gives tare correction values as applied by the computer program to the gross load cell deviation to obtain net values as indicated in a third column 129 of window 260. A new, updated correction value for a specific load cell can be set and stored in the computer memory by activating a corresponding on of buttons "Tare" as shown to the right of window 260. A first column 131 displayed in a second window 261 allows the operator to visualize the current logic "On/Off" status of the various logic inputs received by the computer 190, namely, from PSCs 216, 217, 218, 226, 227, 228 (1–6), limit switches 138, 144, 148 (1–3), PLC line 145 indicating manual lifting, and conveyer signal from PLC 200. A second column 135 displayed in window 261 gives the current cumulative values generated by the input counters associated with each PCS, as well as first and second limit switches 138, 144. Normally, the reading of input counters associated to the PSCs should be at a maximum value if all transverse series of catch blocks are loaded with pieces of lumber, while the input counters associated with first and second limit switches shall be near zero. A third window 262 allows the operator to visualize the current status of the various logic outputs of computer 190 as transmitted to the master PLC 244 and local PLC 200, as explained before. Associated with the logic output displayed a series of "On/Off" buttons 137 that can be selectively activated provided the apparatus is set to "Off" mode, for checking if the selected logic output functions normally. Optionally, the computer program may display a chart (not shown) representing curves of load measurement signal values as a function of time over a predetermined duration corresponding to a complete testing cycle for a given piece of lumber processed, with curves of current logic states of the PLCs and limit switches, to verify synchronicity between load measurement signals and control signals. Such optional function may be useful to adjust the positions of the PSCs and limit switches on first and second deflecting units.

Figure 14:
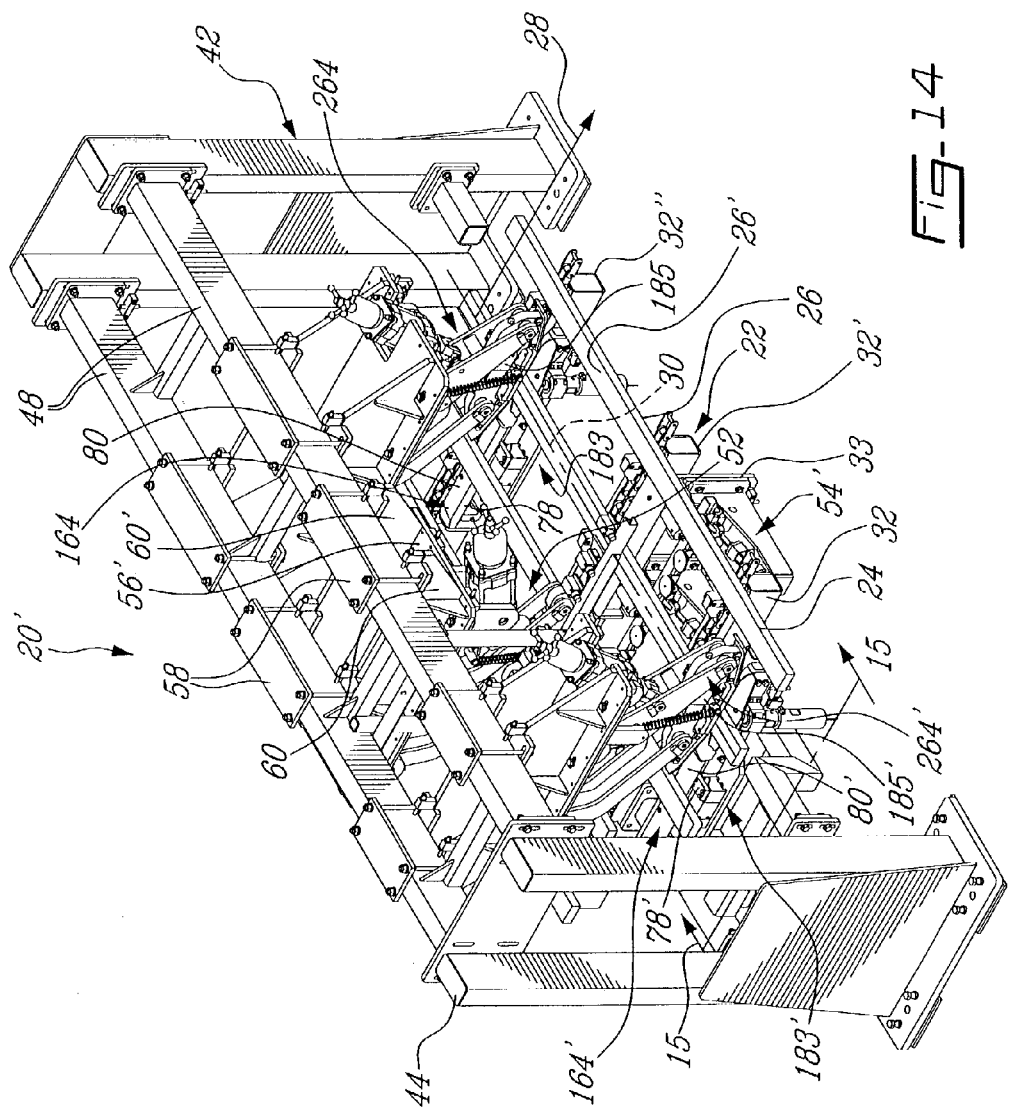
FIG. 14 is a perspective view of the main mechanical components provided on a second preferred embodiment of apparatus according to the present invention.
Figure 15:
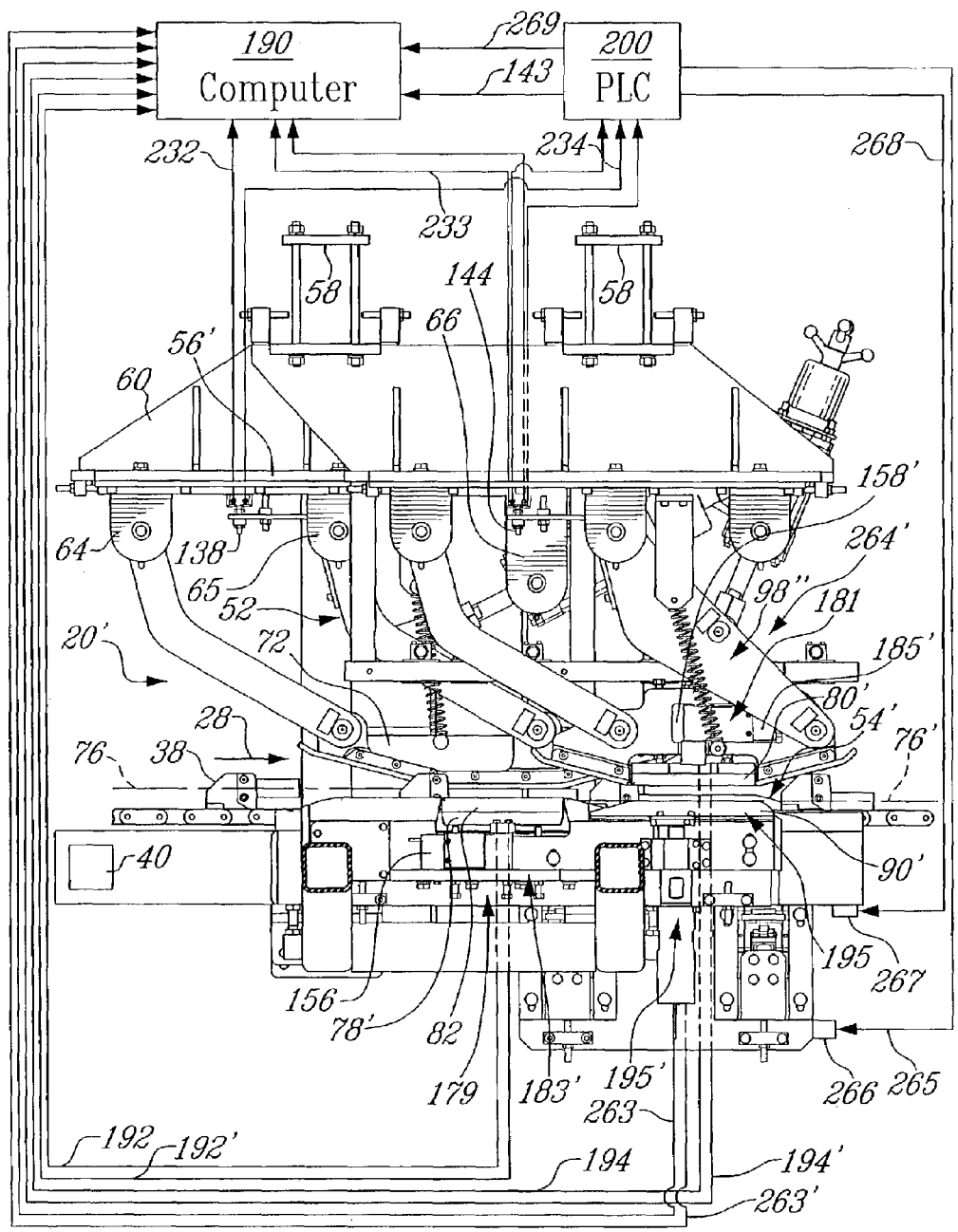
FIG. 15 is a general block diagram of the second embodiment of apparatus according to the invention in relation with a partial cross-sectional elevation view of the main mechanical components according to lines 15—15 of FIG. 14, showing the deflecting units in thrust applying positions on the pieces of lumber under test.

Referring now to FIG. 14, the article testing apparatus according to the second preferred embodiment of the invention and as generally designated at 20' is especially designed to provide reliable stiffness measurement on elongated articles such as pieces of lumber exhibiting different mechanical behavior depending on the feeding orientation through the testing apparatus, mainly due to internal, non-isotropic structure of most wooden materials forming pieces of lumber. In accordance with the second embodiment, there are provided first and second article bearing units capable of contacting first and second article surfaces respectively, the first deflecting unit cooperating with the first article bearing unit for applying the first thrust against the loaded area of the second article surface, while the second deflecting unit cooperates with the second bearing unit for applying the second thrust against the loaded area of the first article surface. The load measuring unit is capable of generating signals indicative of respective magnitudes of the first and second thrusts, from which signals the data processing device is responsive to derive an indication of the stiffness of the article, considering also the first and second deflection magnitudes, as will be explained later in more detail. Since the second embodiment that will now be described makes use of numerous same components as compared to the first embodiment described above with respect to FIGS. 1 to 13, such same components will be designated using same corresponding reference numbers in the following description, and it can be appreciated that the detailed structure and operation of such common components are not needed to be repeated so as to enable a person skilled in the art to reduce the second embodiment to practice in view of the present specification as a whole. The apparatus 20' is adapted for use with the conventional transverse conveying system 22 for transporting a plurality of articles such as pieces of lumber 24 each having opposed main bottom and top surfaces 26, 26', which pieces of lumber 24 move along a predetermined path through apparatus 20' in a conveying direction indicated by arrow 28 substantially transverse to testing axis 30 associated with each piece of lumber 24 along which stiffness will be estimated as described below. The apparatus 20' further includes first and second deflecting units generally designated at 52, 54' as better shown in FIG. 15, in view of FIGS. 17 and 18. The first deflecting unit 52 is adjustably secured to the frame overhead beams 48 using an overhead mounting unit having top mounting plate 56' being maintained in a suspended position using a pair of displaceable attachments 58, with a pair of parallel vertical walls 60, 60'. As shown in FIG. 15, secured to top mounting plate 56' is a bottom mounting plate 62 to which is in turn secured the first deflecting unit 52 using a plurality of pivot members pairs 64, 65, 66 attached to bottom mounting plates 62. The first deflecting unit 52 includes a first working element 72 capable of being disposed in a first, substantially static position shown in FIG. 15 relative to an article conveying path represented by axis 76 and as also presented in FIG. 16B by an axis 73 which is coplanar with axis 76 shown in FIG. 15. It can be seen from FIG. 15 that the first position has been conveniently chosen to be in substantial alignment with the conveying path 76 so as to provide a first deflection value $d_1$ as shown in FIG. 16B and as will be explained later in more detail. The apparatus 20' further includes a first article bearing unit including first and second pairs of rails 78, 78' as shown in FIGS. 15 and 16A for contacting the bottom surface 26 of each piece of lumber 24 under test at two spaced apart portions thereof, as better shown in FIG. 16A. The rails 78, 78' define load bearing surfaces extending substantially parallel to the conveying direction indicated by arrow 28, for contacting the bottom surface 26 at spaced apart portions 77, 77' thereof. The rails 78, 78' are provided with load bearing surfaces 82 for receiving the bottom surface 26 of each piece of lumber 24 when the latter moves past a first location along the conveying path 76 as shown in FIG. 15, at which first location the first deflecting unit 52 is disposed to face the top surface 26' of each piece of lumber 24 under test.

Referring again to FIG. 15 in view of FIG. 14, the first working element 72, when being disposed in the first static position relative to the article conveying path 76 and cooperating with rails 78, 78' of the article bearing unit, is used to apply a first thrust against a loaded area 84 of the top surface 26' of piece of lumber 24 at an intermediary portion located between spaced apart portions 77, 77' as piece of lumber 24 is moving through the apparatus 20', as better shown in FIG. 16A. The thrust applied against loaded area 84 produces a deflection $d_1$ of the piece of lumber 24 of a first magnitude extending along a first deflection axis 86 perpendicular to conveying direction 28 and testing axis 30 as shown in FIG. 16A in view of FIG. 16B. Turning back to FIG. 14, secured to the conveyer frame beam 32' through mounting plate 33, the second deflecting unit 54' is disposed at a location downstream from the corresponding location of first deflecting unit 52, to receive a piece of lumber 24 leaving the thrust applying area defined by the first working element 72 provided on first deflecting unit 52. The second deflecting unit 54' includes a second working element 90' capable of being disposed in a second, substantially static position shown in FIG. 15 relative to conveying path 76' and cooperating with a second pair of spaced apart rails 80, 80' provided on a pair of corresponding spaced apart pushing devices 264, 264' as part of a second article bearing unit and as better shown in FIG. 16A, which devices 264, 264' are disposed to respectively face the top surface 26' of the article at spaced apart portions 77, 77' thereof as also shown in FIG. 16A. The second working element 90' is used to apply a second thrust against a loaded area 94' of bottom surface 26 of piece of lumber 24 at intermediary portion thereof between spaced apart portions 77, 77' as the piece of lumber 24 further moves through the apparatus 20', and as also presented in FIG. 16B by an axis 73' which is coplanar with axis 76' shown in FIG. 15. The second thrust applied against loaded area 94' produces a deflection $d_2$ of piece of lumber 24 of a second magnitude extending along a deflection axis substantially parallel to first deflection axis 86 represented in FIG. 16A. Deflection values $d_1$ and $d_2$, which are of opposite signs as shown by lengthwise profiles of piece of lumber 24 as represented by dotted lines 75, 75' respectively, are preferably set to a same predetermined magnitude, since bow and warp generally do not exhibit predominant orientation amongst pieces of lumber as they are fed to the testing apparatus. It is pointed out that the schematic deflection representation shown in FIG. 16B employs a scale that has been intentionally amplified as compared with actual deflection imparted to a tested piece of lumber for the purpose of illustration. As will be explained later in more detail, absolute values of deflection $d_1$ and $d_2$ are used to derive a resulting deflection parameter D expressed as follows:

$$D_T = |d_1| + |d_2| \tag{14}$$

It is to be understood that according to the second preferred embodiment of the invention, the deflecting unit 52 has been chosen to receive the piece of lumber 24 first so as to produce a deflection of a first, negative magnitude as opposed to positive magnitude $d_2$ obtained when the piece of lumber 24 passes over the second deflecting unit 54' as located downstream from first deflecting unit 52. For so doing, first and second pairs of rails 78, 78' and 80, 80' are disposed in a spaced relationship in the conveying direction so their respective load bearing surfaces 82 sequentially receives corresponding first (bottom) and second (top) contacted surfaces 26, 26' of article 24 when it moves past first and second locations along the article conveying path. However, the respective position of first and second working elements 72, 90', and associated bearing units may be alternatively set so that the deflection of positive magnitude $d_2$ be measured first, followed by the measurement of the deflection of negative magnitude $d_1$. Moreover, while first and second deflecting units 52, 54' are preferably aligned in a spaced apart relationship along the conveying direction so to apply their respective thrust on a same loaded area, other configurations may involve distinct loaded areas, insofar reliable measurements are obtained.

Turning now to FIG. 17 in view of FIG. 5, it can be seen that the first deflecting unit 52 provided on the second embodiment includes a displaceable mechanism 98 essentially identical to the one included in the first deflecting unit provided on the first embodiment that has been described in detail above, and is adapted to perform the same function of holding the first working element 72, and more particularly of providing selective controlled movement of the working element 72 between the first substantially static position as described above with respect to FIGS. 15 and 16B relative to the conveying path indicated by axis 76, 76' on FIG. 15, and a retracted position wherein the first working element 72 is away from the article conveying path to prevent obstruction thereof. The displaceable mechanism 98 may be provided with a pair of tension springs 71 extending between a member 79 secured to the bottom mounting plate 62, and the first working element 72, for ensuring that the latter maintain its working position during operation. It can be appreciated that similar springs may be advantageously installed on the deflecting unit 52 provided on the first embodiment as described above in view of FIG. 5. Turning again to FIG. 17, the first working element 72 defines a loading surface 124 extending substantially parallel to the conveying path when disposed in the first static position. Preferably, the dimension of the loading surface 124 parallel to the conveying direction is larger than the transverse dimension of the piece of lumber 24 at the intermediary portion thereof extending between end portions 77, 77' shown in FIG. 16A, so that the loaded area 84 substantially extends over the whole transverse dimension while the thrust magnitude indicating signals are generated, in a same manner as explained before in respect of the first embodiment. It can be seen from FIG. 17 that the working element 72 preferably defines an article feed guiding surface 150 generally extending toward the loading surface 124 according to an appropriated acute angle $\beta_1$ with respect to the conveying path at 76, according to a similar design as applied to the first working element of the first embodiment shown in FIG. 5. However, the first working element 52 according to the second embodiment is further provided with a symmetrical article output guiding surface 152' presenting an angle $\theta_1$ with respect to conveying path at 76 the value of which angle $\theta_1$ being typically set to about 15° according to a similar design as applied to the second working element 90 provided on the first embodiment shown in FIG. 5. Such output guiding portion is provided since first and second deflecting units 52, 54' are not located in adjacent relationship according to the second embodiment. The loading surface 124 provided on first working element 72 preferably has first and second symmetrical portions 126, 128 also extending toward respective spaced apart portions 77, 77' of piece of lumber 24 transversely to the conveying direction according to a symmetrical angle $\alpha_1$ defined by axis 136 on FIG. 17 which extends from surface loading portion 128 and with respect to an axis 30' parallel to testing axis 30 shown in FIG. 16A, which symmetrical angle $\alpha_1$ being substantially proportional to the first deflection magnitude $d_1$ along axis 86 of FIGS. 16A and 16B, which is parallel to axis 132, 134 shown in FIG. 17. Similarly to the first embodiment, the first displaceable mechanism 98 is provided with a third position sensor in the form of a third limit switch 148 for generating a third control signal whenever the first working element 72 substantially departs from the first static position by a third predetermined overload threshold greater than the above-mentioned first overload threshold as a result of the departure of the piece of lumber 24 from its normal conveying position on rails 78, 78'.

Turning now to FIG. 18, the second deflecting unit 54' provided on the second embodiment includes a further displaceable mechanism 99 for holding the second working element 90'. The mechanism 99 is preferably of a two-position latch type that is selectively controllable to move the second working element 90' between the second, substantially static, locking position relative to conveying path 76' as shown in FIG. 15 and a retracted, release position (not shown) wherein the second working element 90' is away from the article conveying path to prevent obstruction thereof, in case of abnormal feeding position of article or for maintenance purpose as will be explained later in more detail. The displaceable mechanism 99 preferably comprises a pair of latch assemblies 151 secured to the mounting plate 33 as also shown in FIG. 14, each assembly 151 comprising a lifting platform 153 secured to a first pivoting element 155 that is in turn coupled to a linking element 157 having an ear 159 pivotally attached to the piston 161 of a hydraulic actuator 163 secured to the body of the corresponding latch assembly 151. Each hydraulic actuator is fed by fluid pressure through hydraulic lines (not shown) connected to the output of a reversing valve 266 shown in FIG. 15 that is controlled by PLC 200 through control line 265. The PLC 200 is also used to send through line 269 an enabling signal to the computer 190 whenever the second working element 90' in its working position. The linking element 157 provided on each latch assembly 151 is also coupled to a second pivoting element 165 also secured to the body of the corresponding assembly 151. Mounted on the lifting platform 153 is the second working element 90' in the form a multi-level rail defining a receiving portion 167, a setting portion 169 and a loading surface 171 extending substantially parallel to the article conveying path when disposed in the second substantially static position. Preferably, the dimension of the loading surface 124 parallel to the conveying direction is larger than the transverse dimension of the piece of lumber 24 at the intermediary portion thereof extending between end portions 77, 77' shown in FIG. 16A, so that the loaded area 84 substantially extends over the whole transverse dimension while the thrust magnitude indicating signals are generated, in a same manner as explained before in respect of the first embodiment. Turning back to FIG. 18, the second working element 90' further defines an output portion 173 in the form of a declining ramp, causing release of the second thrust applied against the loaded area 84 shown in FIG. 16A, as the piece of lumber 24 further moves through the apparatus, toward the second deflecting unit that will be described later. The second working element 90' is preferably mounted onto the lifting platforms 153 using a pair of tilting devices 175, 175' allowing position adjustment of the loading surface 171 with respect to the conveying path in direction 28. Tilting devices 175,175' include conventional rotary-to-linear actuators 177, 177' coupled to linear tooth racks (not shown) secured to corresponding platforms 153, and a pair of displaceable members (not shown) to which front and rear portions of the working element 90' are respectively attached. The selective operation of tilting devices 175, 175' by the operator provides the desired position adjustment.

Turning back to FIG. 15, the apparatus 20' according to the second embodiment further includes first and second load measuring units generally designated at 179, 181 and respectively associated with first and second deflecting units 52, 54'. The first load measuring unit 179 is formed by a pair of right and left sides subunits 183, 183' mechanically coupled to first and second rails 78, 78' of the first bearing unit as shown in FIG. 14, and the second measuring unit 181 is formed by a similar pair of right and left sides subunits 185, 185' mechanically coupled to the pushing devices 264, 264' provided on the second bearing unit as will be described later in more detail. Load measuring units 179, 181 are capable of generating signals indicative of respective magnitudes of first and second thrusts as applied by first and second deflecting units 52, 54' as will be later explained in more detail.

Turning now to FIG. 19, first (right) rail 78 as part of the first article bearing unit is shown with a corresponding load measuring subunit 183 according to the second embodiment. Since subunits 183, 163' are identical, the description below will be limited to the right side subunit 183, which preferably makes use of a single load sensor using load cell 156 having load coupling members 160 receiving rail 78 in rigid connection thereto. It can be seen that the load measuring subunit 183 does not necessarily require that the guiding means be adjacently disposed with respect to rail 78 in an offset, parallel configuration provided on the first embodiment and depicted in FIG. 7. As shown in FIG. 19, a linear configuration may be employed wherein rail 78 is aligned with the guide member 164, using a load cell supporting plate 166 of an appropriate design. The guide member 164 is rigidly secured to conveyor frame beam 32" in a same manner as described before in respect of the first embodiment in view of FIGS. 4 and 7. However, it can be seen from FIG. 14 that the linear configuration allows to use a same design for load measuring subunits 183, 183' and guide members 164, 164', provided specific transverse angular profile is adapted. It can be seen from FIG. 19 in view of FIG. 14 that each guide member 164, 164' is disposed relative to the article conveying path represented by axis 76 in FIG. 17 in the conveying direction at 28 to set the piece of lumber 24 on the load bearing surface 82 of rails 78, 78' as the piece of lumber 24 moves through the apparatus 20'. The elongate guide members 164, 164' are disposed in a parallel spaced relationship and longitudinally extend in the conveying direction 28 as shown in FIG. 14. As explained before in respect of the first embodiment in view of FIGS. 4 and 7, each load bearing surface 82 defined by rails 78, 78' longitudinally extends along the conveying path in conveying direction 28, while extending toward the intermediary portion of the piece of lumber 24 transversely to the conveying direction according to a angle $\gamma_1$ with respect to the testing axis 30' which is parallel to testing axis 30 of FIG. 16A, which angle $\gamma_1$ is substantially proportional to the first deflection magnitude $d_1$ for rails 78, 78, corresponding typically to an angular value of about 1°. Such angular feature allows each load bearing surface 82 to follow the shape of corresponding contacted article surface when the article moves past the first thrust applying location along the article conveying path. Each guide member 164, 184' has a guide element 172' defining an article setting portion 180 disposed upstream corresponding rails 78, 78' in an adjacent relationship therewith to set a piece of lumber onto load bearing surface 82 when the piece of lumber moves past the location of first deflecting unit 52 shown in FIG. 14. As shown in FIG. 19, the guide element 172' has a receiving portion 176 disposed upstream article setting portions 180. The setting portion 180 of guide element 172' extends toward the intermediary portion of piece of lumber 24 transversely to the conveying direction 28 according to angle $\gamma_1$ with respect to axis 30'. Each guide member 164, 164' includes a further section 187 having a declining ramp portion 191 disposed to receive each article leaving the load bearing surface 82, followed by a lower level portion 193 providing sufficient clearance to the article end portions as the article reaches the second location along the conveying path where it is subjected to the second thrust applied by the second deflecting unit 54' cooperating with the pushing devices 264, 264' provided on the second bearing unit. As also shown in FIGS. 15 and 19, the testing apparatus 20 is preferably provided with a profile sensing device conveniently formed by a pair of presence sensors 195, 195' disposed within the article conveying path for providing a signal indicative of the twist characterizing the article, whose level may have an effect on the stiffness measurement derived by the data processing device as will be explained later in more detail. Each presence sensor 195, 195' is disposed at the further section 187 of a corresponding one of guide member 164, 164' and includes a body 197 secured to the guide member, a pneumatic cylinder 199 provided with a piston 201 connected to a movable platform 213 defining a contacting member 215. Each cylinder 199 is fed by fluid pressure through pneumatic lines (not shown) connected to the output of a reversing valve 267 shown in FIG. 15 that is controlled by PCL 200 through control line 268, allowing the contacting member 215 to be moved between an upper, presence detecting position and a lower, disable position. A guide rod cooperating with a corresponding bore extending through the body 197 allow a vertical displacement of the platform with respect to the body 197, while maintaining alignment of the platform with respect to the guide member section 187 in the conveying direction. Disposed adjacent the piston to sense the stroke thereof is a displacement sensor 250 such as ultrasonic probe model no. M18C2 from Banner Engineering carp. (Minneapolis, Minn, U.S.A.) for generating a twist indicating signal toward the computer through line 263', as also shown in FIG. 15 on which are illustrated a further line 263 coming from presence sensor 195 associated with guide member 164, along with lines 192, 192' and 194, 194' sending to computer 190 the applied thrust magnitude indicative signals generated by pairs of load cells 156 as described before, as well as by pair of load cells 158' as part of the second article bearing unit that will be now described in more detail.

Referring now to FIG. 20, the pushing device 264 is shown, which is identical to the pushing device 264' completing the second article bearing unit. The pushing device 264 includes second displaceable mechanisms 98', 98" of a similar design as compared with the displaceable mechanism 98 provided on the deflecting unit 52 described hereinabove in view of FIG. 17, wherein the actuator 108' is preferably mounted under the bottom plate 56' secured to top mounting plate 56", 62' through a cut provided thereon as better shown in FIG. 14, to present a higher rake within the vertical plane, thereby increasing the effective thrust applying capacity of the pushing device 264. The pneumatic actuator 108' is also provided with a mechanism 123' for adjusting the limit stroke of piston 110' using rotary handle 125' provided thereon, allowing accurate adjustment of the thrust applying position of the pushing device 264. It can be seen from FIG. 20 in view of FIG. 17 that the double member 100' has been strengthened accordingly as compared with the double member actuator 100' provided on the mechanism shown in FIG. 17. As part of the second article bearing unit, the displaceable mechanisms 98', 98" are used to hold a second pair of spaced apart rails 80, 80' as load bearing elements defining load bearing surfaces 82 extending substantially parallel to the conveying direction for contacting the second, top article surface at spaced apart portions 77, 77' thereof, as explained above with reference to FIG. 16A. As mentioned before with respect to FIG. 15, the second measuring unit 181 is formed by a pair of right and left sides subunits 185, 185' mechanically coupled to the pushing devices 264, 264', and includes a pair of load sensors 158 operatively coupled to the pushing devices by incorporating them within a compartment defined in a end support member 93 pivotally connected to the double members 100', 116' provided on each mechanism 98', 98". Each subunits 185,185' includes a load coupling members 162' for holding rail 80 in rigid connection thereto. Also as part of the load measuring are guide means in the form of input and output guide members 87, 87' provided on each subunits 185, 185' and respectively disposed upstream and downstream corresponding rails 80, 80' in an adjacent relationship therewith along the article conveying path to set the article on the load bearing surfaces 82, and to guide the article out of the testing area as the article moves forward. The input guide member 87 preferably defines an article feed guiding surface 150' generally extending toward the load bearing surface 82 according to an appropriated acute angle $\beta_2$ with respect to the conveying path at 76', while the output guide member 88 symmetrically defines an article output guiding surface 152' presenting an angle $\theta$ with respect to conveying path at 76' the value of which angle $\theta$ being typically set to about 15°. Each load bearing surface 82 defined by rails 80, 80' longitudinally extends along the conveying path indicated by axis 76', while extending toward the intermediary portion of the piece of lumber 24 transversely to the conveying direction according to a angle $\gamma_2$ with respect to the testing axis 30" which is parallel to testing axis 30 of FIG. 16A, which angle $\gamma_2$ is substantially proportional to the second deflection magnitude $d_2$ for rails 80, 80', corresponding typically to an angular value of about 1°. As explained before, such angular feature allows each load bearing surface 82 to follow the shape of corresponding contacted article surface when the article moves past the second thrust applying location along the article conveying path. It can be appreciated from FIGS. 19 and 20 in view of FIG. 14 that first and second pairs of spaced apart guide elements 180 and 87 are disposed to sequentially set the article on corresponding load bearing surfaces 82 when the article moves past the first and second thrust applying locations along the article conveying path. Similarly to the displaceable mechanisms 98' described above in view of FIG. 5, the displaceable mechanisms 98',98" shown in FIGS. 15 and 20 are selectively controllable to move the support member 93 and rails 80, 80' between a thrust applying position adjacent article conveying path indicated by axis 76 in FIG. 20 and a retracted position similar to the position shown in FIG. 6 with respect to the first embodiment, wherein sets of guide members 87,88 and each associated rail 80,80' are brought away from the conveying path to prevent obstruction thereof. As explained before with respect to the first embodiment, the second limit switch 144 generates a second control signal whenever the associated rail 80,80' departs from the thrust applying position by a second predetermined overload threshold as a result of the departure of piece of lumber 24 from its normal conveying position onto the rails 80, 80' as shown in FIG. 15, the computer 190 being responsive to that second control signal to cancel the derivation of article stiffness indication in a same manner as explained before with respect to the first preferred embodiment. Moreover, the controller provided in the apparatus is responsive to the third control signal generated by the third limit switch 148 provided on the first mechanism described before in view of FIG. 17, to cause the first displaceable mechanism 98 to move the first working element 72 from the first static position to its retracted position, and to cause each second displaceable mechanism 98',98" to move each load bearing rail 80,80' from its working position to its retracted position. Preferably, second displaceable mechanism 98', 98" are respectively provided third and fourth position sensor in the form of further limit switches 148' as shown in FIG. 20, which cooperate with double-switch block 140 to generate fourth and fifth control signal whenever any of rails 80, 80' substantially departs from their respective thrust applying positions by a further predetermined overload threshold greater than the above-mentioned second overload threshold as a result of the departure of the piece of lumber 24 from its normal conveying position in contact with rails 80,80'. Furthermore, as described before with respect of the first embodiment in view of FIG. 2, a presence sensor 236 disposed upstream from the first thrust applying location may be also used to detect any article significantly departing from the predetermined conveying position while moving in the conveying direction, to generate a further control signal directed to the controller, the latter being further responsive to that control signal to cause the first displaceable mechanism 98 shown in FIG. 17 to move the first working element 72 from the first static position to its retracted position, to cause each second displaceable mechanism 98',98" to move each corresponding load bearing rail 80,80' from its working position to its retracted position, and to cause the displaceable mechanism 99 shown in FIG. 18 to move the second working element 90' from the second static position to its retracted position. Moreover, while deflecting units 52, 54' may be manually returned to their respective first and second static positions shown in FIG. 15 using a manual selector (not shown) provided on the apparatus, it preferably uses the displacement indicating signal generated by the encoder 40 and continuously sent to the PLC 200, to verify that the transverse series of catch blocks 38 associated with an improperly positioned piece at the origin of the actual or expected overload error condition has been displaced beyond the load applying zone of the second deflecting unit 54', and to command PLC 200 to move back displaceable mechanisms 98, 98' and 99 so as to move first and second working elements 72, 90 from their respective retracted positions to respective first and second static positions and to move each load bearing rail 80, 80' from its retracted position to its working position as shown in FIG. 15.

Prior to the operation of the apparatus 20', first and second static positions of first and second working elements 72 and 90' are respectively set using adjustment mechanism 123 provided on actuator 108 as shown in FIG. 17, and tilting devices 175, 175' a shown in FIG. 18. An appropriate adjustment of the thrust applying position of the pushing device 264 is also made using mechanism 123' shown in FIG. 20. Typically, on the basis of equation (14) above, the working elements 72, 90' are positioned so as to have a first deflection nominal value $d_{n1}=-1,9$ cm and to have a second deflection nominal value $d_{n2}=1,9$ cm to obtain a resulting value for $D_T$ close to a nominal value $D_n=3,8$ cm, after applying correction factors as will be described later in detail.

Figure 21A:
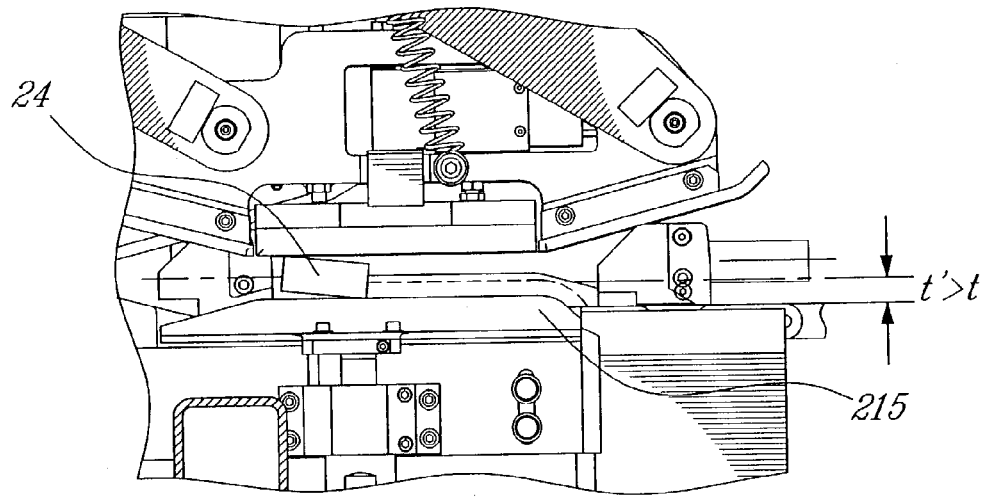
FIGS. 21A and 21B are partial elevation view of the embodiment of FIG. 14 showing operation of the profile sensing device used to generate twist indication that may advantageously used for stiffness estimation.
Figure 21B:
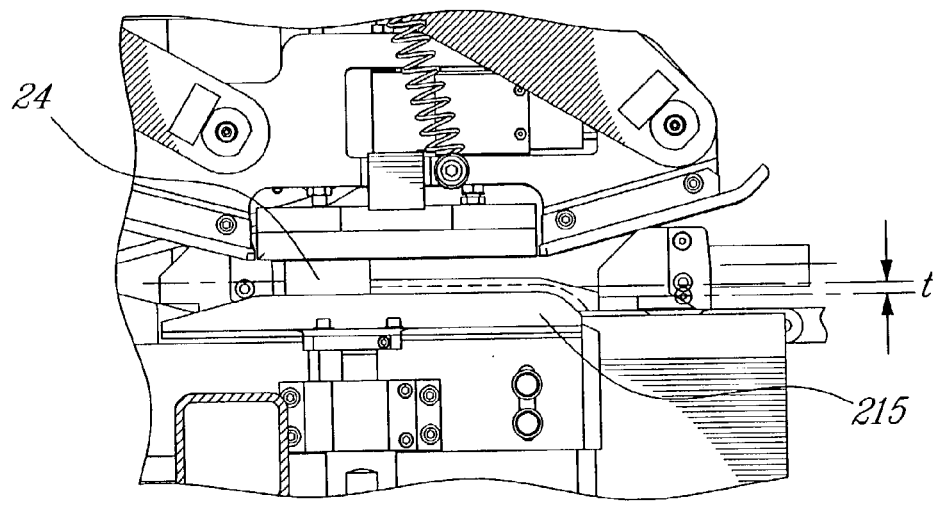

The mode of operation of the second embodiment of the present invention is in most part identical to the operation mode explained before with respect to the first embodiment, with some variations due to the additional components provided at the second testing location, and due to the use of the profile sensing device. Referring to FIG. 19, after leaving the load bearing surface 82 of first pair of rails 78, 78', the piece of lumber 24 reaches the declining ramp portion 191 to progressively enter within the thrust applying and load measuring zone defined by the second working element 90' of the second deflecting unit 54' and corresponding pair or rails 80, 80' mounted on the pushing devices 264, 264'. Then, the piece of lumber 24 intersects the detecting beam of photo-sensitive cell 226 as part of the second presence sensor as explained before in view of FIG. 2, causing the generation of a control signal sent to the computer 190 for triggering data acquisition of load measurement signals from the second pair of load cells 158, 158' transmitted to the computer 190 through lines 194, 194' as shown in FIG. 15. Simultaneously, the leading end of tested piece 24 reaches the front end of contacting member 215 provided on each presence sensor 195, 195' as part of he profile sensing device and as shown in FIG. 19, which sensors 195,195' have been previously set by PLC 200 through line 268 to their presence detecting position as better shown in FIGS. 21A and 21B. It can be seen that the uppermost limit position of each contacting member 215 is initially set to ensure that every piece 24 makes contact with it, no matter its specific profile. In the example shown in FIG. 21B, it can be seen that the displacement induced by the article 24 to the contacting member 215 with respect to its reference initial level indicated in dotted lines, which displacement is associated with an extra thickness value corresponding to a low twist level, is not greater that threshold t under which the torsion level is not considered as significant, as will be explained later in more detail with reference to equations (26) and (27). Referring to FIG. 21B, it can be seen that the displacement or extra thickness t' has a magnitude greater than threshold t, so that the resulting twist indication signal generated by the ultrasonic probe integrated in the profile sensor through lines 263, 263' shown in FIG. 15, will be preferably used by the computer 190 to derive article stiffness indication, as will be now explained in detail. When data acquisition is completed, the computer program automatically starts calculation of the modulus of elasticity value associated with each tested piece of lumber 24 according to a process that will be now described below.

First, a mean load measurement value is calculated for each load cell as follows:

$$RawLoad[i] = \left(\frac{\sum_{j=1}^{n} \text{Load}[i][j]}{n}\right) * K_{kg} \quad (15)$$

with: Load = Voltage − 0.5 wherein:

i is a cell identification indicia, with i=1,2 indicating the load cells 156 coupled to the first pair of rails 78, 78' and associated with the first deflecting unit 52, while i=3,4 indicating the load cells 158 coupled to the second pair of rails 80, 80' and associated with the second deflecting unit 54';

n is the number of load measurement data samples read;

$K_{kg}$ is a predetermined factor (kg/Δvolt) for converting the measurement in kg unit;

Load is a corrected load measurement voltage generated by each load cell 156 as corrected by a predetermined offset value characterizing the load cell when unloaded.

Then, the obtained value for RawLoad[i] is preferably corrected using a predetermined tare correction value to compensate for the output level drift to which each load cell is subjected with time, the value of which can be measured when no load is applied to the load cell. The offset value can be established through an initial or periodic manual calibration procedure. The computer calculates a corrected or net load measurement value from the estimated tare value for each load cell of indicia i as follows:

$$\text{NetLoad}[i] = \text{RawLoad}[i] + \text{Tare}[i] \quad (16)$$

Then, the computer program calculates the load applied by each deflecting unit 52, 54' as well as a total applied load value as follows:

$$\text{NetLoad}D_1 = \text{NetLoad}_1 + \text{NetLoad}_2 \quad (17)$$

$$\text{NetLoad}D_2 = \text{NetLoad}_3 + \text{NetLoad}_4 - 2*\text{Thrust}P \quad (18)$$

$$\text{Load}_T = \text{NetLoad}D_1 + \text{NetLoad}D_2 \quad (19)$$

wherein:

$\text{NetLoadD}_1$ is the net load value applied by the first deflecting unit 52 imparting the first, negative sign deflection magnitude $d_1$; and $\text{NetLoadD}_2$ is the net load value applied by the second deflecting unit 54' imparting the second, positive sign deflection magnitude $d_2$;

ThrustP is the thrust value applied by each presence sensor 195,195'; and $\text{Load}_T$ is the total applied load value.

On the basis of the above calculations, according to a similar approach used for the first embodiment, the computer preferably applies a correction to the nominal deflection values as set prior to the operation of the apparatus, to compensate the inherent deformation to which the whole structural components of the apparatus are subjected, such as flexion of load cells 156,158, overhead beams 48, first deflecting unit 52 and pushing devices 264, 264' associated with second deflecting unit 54'.

The correction is made on the basis of estimated deflection error values associated with first and second deflection values $d_1$, $d_2$ as calculated as follows:

$$ErD_1 = \left(\frac{NetLoad_1}{2}*K_{Cell1}\right) + \left(\frac{NetLoad_2}{2}*K_{Cell2}\right) + \left(InD_1\frac{TwistD_1}{2}\right) \quad (20)$$

$$ErD_2 = \left(\frac{InD_{2LeftPush} + InD_{2RightPush}}{2}\right) - \left(\frac{TwistD_2}{2}\right) \quad (21)$$

with:

$$InD_1 = KS_{1,1}*(NetLoad_1+NetLoad_2)+KS_{2Left,1}*NetLoad_3+KS_{2Right,1}*NetLoad_4+K_{1,1}*(NetLoad_1+NetLoad_2) \quad (22)$$

$$InD_{2LeftPush} = KS_{1,2Left}*(NetLoad_1+NetLoad_2)+KS_{2Left,2Left}*NetLoad_3+KS_{2Right,2Left}*NetLoad_4+K_{2,2}*NetLoad_3 \quad (23)$$

$$InD_{2RightPush} = KS_{1,2Right}*(NetLoad_1+NetLoad_2)+KS_{2Left,2Right}*NetLoad_3+KS_{2Right,2Right}*NetLoad_4+K_{2,2}*NetLoad_4 \quad (24)$$

$$TwistD_2 = \frac{ExThick_{Left} + ExThick_{Right}}{2} \quad (25)$$

$$ExThick_{Left} = RawThick_{Left} + InD_{2RighPush} - NomThick$$
with $ExThick_{Left} \geq t$ \quad (26)

$$ExThick_{Right} = RawThick_{Right} + InD_{2RightPush} - NomThick$$
with $ExThick_{Right} \geq t$ \quad (27)

$$TwistD_1 = TwistD_2' - (TwistD_2' - TwisTD_2) * \frac{(NetLoad_1 + NetLoad_2)}{(NetLoad_3 + NetLoad_4)} \quad (28)$$

$$TwistD_2' = ((\sin \Delta\tau)*NomWidth) + TwistD_2 \quad (29)$$

$$\Delta\tau = \left(\left(NomWidth * \left(\frac{(NetLoad_3 + NetLoad_4)}{2}\right)\right) * \left(\frac{S}{2}\right)\right) / (T * I_T) \quad (30)$$

$$T = \frac{NomWidth}{2} * \left(\frac{NomThick}{2}\right)^3 * \left(\frac{16}{3} - \left(3.36 * \frac{NomThick}{NomWidth}\right) * \left(1 - \left(\frac{NomThick^4}{12*NomWidth^4}\right)\right)\right) \quad (31)$$

wherein:

$K_{cell1}$ is a predetermined constant factor (N*m) representing stiffness characterizing load cell 156 coupled to rail 78 and corresponding load measuring subunit 183;

$K_{cell2}$ is a predetermined constant factor (N*m) representing stiffness characterizing load cell 156 coupled to rail 78' and corresponding load measuring subunit 183';

$InD_1$ represents intrinsic deflection induced to first deflecting unit 52 when a piece is passing through the first testing location;

$InD_{2LeftPush}$ represents intrinsic deflection induced to left pushing device 264 when a piece is passing through the second testing location;

$InD_{2Rightpush}$ represents intrinsic deflection induced to right pushing device 264' when a piece is passing through the second testing location;

$TwistD_1$ represents deflection of the piece induced by its inherent twist when the piece is passing under thrust through the first testing location;

$TwistD_2$ represents deflection of the piece induced by its inherent twist when the piece is passing under thrust through the first testing location as estimated from thickness measurements provided by presence sensors 195,195';

$KS_{1,1}$ is a predetermined constant factor (N*m) representing stiffness characterizing the structural components of the frame including beams 48 just above the first deflecting unit 52, when the latter is applying a thrust against a piece at the first testing location;

$KS_{2Left,1}$ is a predetermined constant factor (N*m) representing stiffness characterizing the structural components of the frame including beams 48 just above the first deflecting unit 52, when the left pushing device 264 is applying a thrust against a piece at the second testing location;

$KS_{2Right,1}$ is a predetermined constant factor (N*m) representing stiffness characterizing the structural components of the frame including beams 48 just above the first deflecting unit 52, when the right pushing device 264' is applying a thrust against a piece at the second testing location;

$K_{1,1}$ is a predetermined constant factor (N*m) representing stiffness characterizing the first deflecting unit 52, when the latter is applying a thrust against a piece at the first testing location;

$KS_{1,2Left}$ is a predetermined constant factor (N*m) representing stiffness characterizing the structural components of the frame including beams 48 just above the left pushing device 264, when the first defecting unit 52 is applying a thrust against a piece at the first testing location;

$KS_{2Left,2Left}$ is a predetermined constant factor (N*m) representing stiffness characterizing the structural components of the frame including beams 48 just above the left pushing device 264, when the latter is applying a thrust against a piece at the second testing location;

$KS_{2Right,2Left}$ is a predetermined constant factor (N*m) representing stiffness characterizing the structural components of the frame including beams 48 just above the left pushing device 264, when the right pushing device 264' is applying a thrust against a piece at the second testing location;

$K_{2,2}$ is a predetermined constant factor (N*m) representing stiffness characterizing the first deflecting unit 52, when the latter is applying a thrust against a piece at the first testing location, which factor includes stiffness characterizing load cells 156 coupled to rails 80,80' and corresponding load measuring subunits 185,185'.

$KS_{1,2Right}$ is a predetermined constant factor (N*m) representing stiffness characterizing the structural components of the frame including beams 48 just above the right pushing device 264', when the first defecting unit 52 is applying a thrust against a piece at the first testing location;

$KS_{2Left,2Right}$ is a predetermined constant factor (N*m) representing stiffness characterizing the structural components of the frame including beams 48 just above the right pushing device 264', when the left pushing device 264 is applying a thrust against a piece at the second testing location;

$KS_{2Right,2Right}$ is a predetermined constant factor (N*m) representing stiffness characterizing the structural components of the frame including beams 48 just above the right pushing device 264, when the latter is applying a thrust against a piece at the second testing location;

$EfThick_{Left}$ represents the effective thickness as measured by left presence sensor 195 as part of the profile sensing device;

$RawThick_{Left}$ represents the raw thickness as measured by left presence sensor 195 as part of the profile sensing device;

NomThick represents a predetermined nominal value for the thickness of pieces under test;

NomWidth represents a predetermined nominal value for the width of pieces under test;

$ExThick_{Right}$ represents the extra thickness as measured by right presence sensor 195' as part of the profile sensing device;

RawThick$_{Right}$ represents the raw thickness as measured by right presence sensor 195' as part of the profile sensing device;

t is the predetermined threshold value under which twist is considered as non-significant;

TwistD$_2$' represents deflection of the piece induced by its inherent twist when the piece is passing without trust through the first testing location as estimated from twist module K$_T$ and related inertia module I$_T$;

Δτ represents twist angle variation under thrust applied at the second testing location;

S is the span extending between the load bearing surfaces 82 of each pair of rails 78, 78' and 80, 80';

Then, on the basis of the above error estimates, a total net deflection value considering first and second deflections induced with applied corrections is derived as follows:

$$D_T = d_{n1} - ErD_1 + d_{n2} - ErD_2 \quad (32)$$

wherein:

d$_{n1}$ represents a predetermined nominal value (ex. 0.75 in) for the deflection induced by the first deflection unit 52;

d$_{n2}$ represents a predetermined nominal value (ex. 0.75 in) for the deflection induced by the second deflection unit 54'.

Then, the computer proceed with calculation of a raw modulus of elasticity for the tested piece according to the following relations:

$$RawE = \frac{Load_T \times S^3}{48 \times I \times D_T} \text{ with:} \quad (33)$$

$$I = \frac{W \times T}{12} \text{ wherein:} \quad (34)$$

I is the inertia modulus value for a tested piece having rectangular section;

W is the transverse width dimension (in cm) of the tested piece; and

T is the thickness dimension (in cm) of the tested piece.

Figure 22:
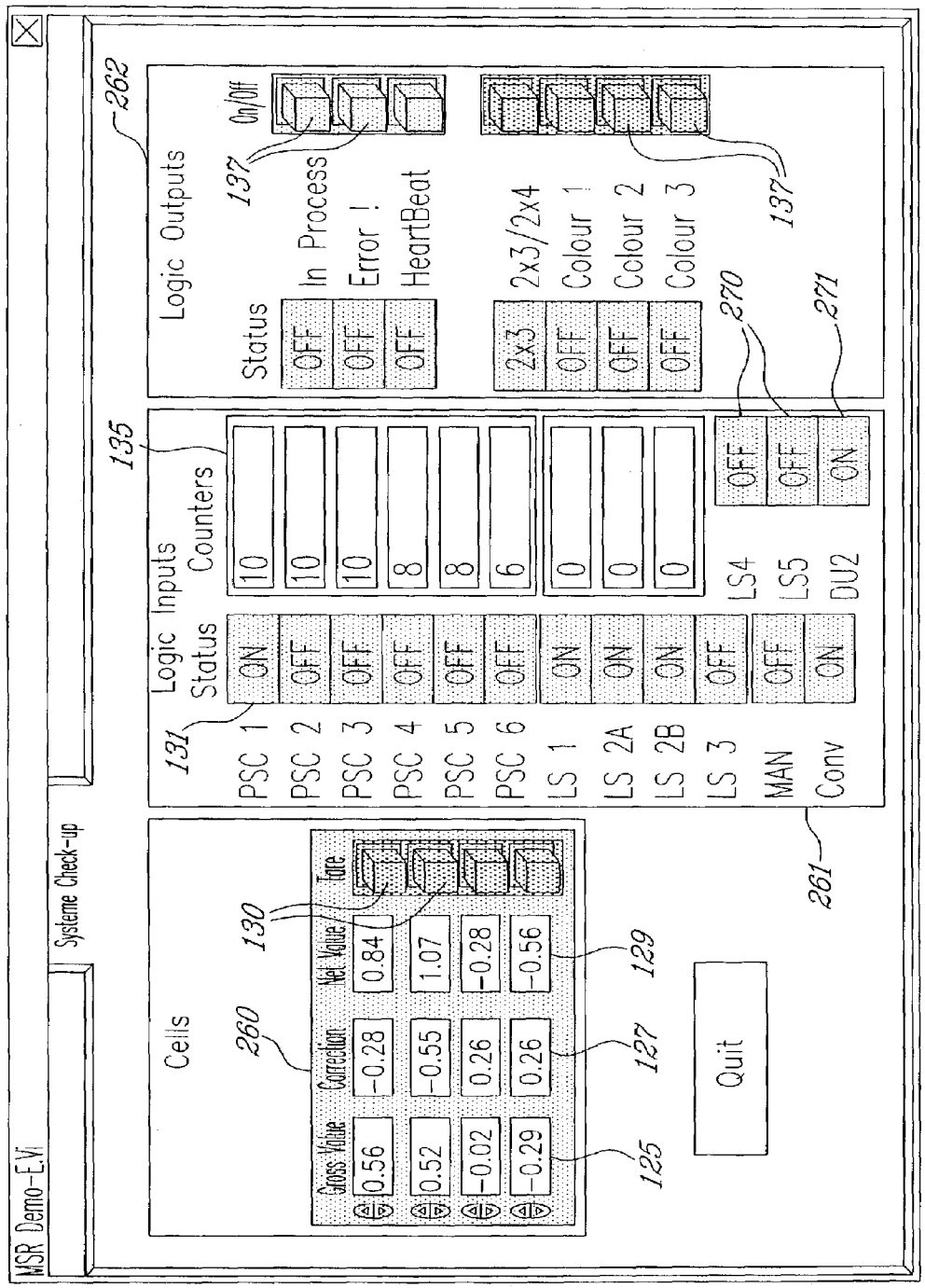
FIG. 22 is a representation of a "System Check-up" screen of the computer display interface provided for the operator, showing some extra fields.

From the raw modulus of elasticity obtained, the computer program then applies dynamic and static edge corrections, in a same manner as explained before in view of equation (13). Finally, the tested piece of lumber 24 is further advanced through the action the catch blocks 38 past the rail output portion 173 provided on the second working element 90' as better shown in FIG. 18, toward the apparatus output, while the computer performs the classification of the tested piece according to the associated resulting net E through a comparison with a predetermined threshold value, in a same way as explained before regarding the first preferred embodiment. The computer also performs the various functions explained above, including tare monitoring function, PSCs status monitoring function and overload detection monitoring function involving extra limit switches 148', in essentially the same way as explained before regarding the first embodiment. As to the computer display interface provided for the operator, similar display screens such as those illustrated in FIGS. 8 to 12 can be implemented by the computer software with some extra fields in the "System Check-up" screen shown in FIG. 22, wherein further indicators are included within first column 131 of second window 261 allowing the operator to visualize the current logic "On/Off" status of the logic inputs received by the computer 190 from limit switches 144 (LS2a, LS2b) provided on both pushing devices 264, 264' with corresponding counters in second column 135. A further column including status indicators 270 for extra limit switches 148' is also provided, also including an indicator 271 specifying whether the second deflecting unit is its working position or not.

It is to be understood that the stiffness testing apparatus and method according to invention is not limited to the specific embodiments described above, and that obvious variants may be implemented without departing from the scope of the invention. For example, as to the first embodiment, the support unit may be formed by a single pair of spaced apart rails rather than two pairs of rails as described before, so as to use a single corresponding pair of load cells to generate load measurement signals as the piece under test successively passes through first and second testing zones under first and second deflecting units. Moreover, to test longer workpieces (12–16 feet lumber) with more accuracy, a plurality of workpiece bearing units capable of contacting the workpiece at more than two spaced apart portions along the workpiece to define complementary transverse spans may be provided, using corresponding additional deflecting units and load measuring units. Furthermore, the apparatus may be readily modified so as to convey the piece of lumber in a direction parallel to its edge surfaces so as to apply the load to an edge rather than to a main surface of the piece of lumber, in which case the static correction factor K$_{Stat}$ referred to above would be no longer necessary. Moreover, it is to be understood that depending upon material characteristics and dimensions of the specific product to be tested, other conveying and load applying approaches may be used, which may involve mechanical devices disposed in different positions with respect to horizontal or vertical plane, provided the relative position between load measuring and load applying devices allows reliable stiffness testing.

What is claimed is:

1. An apparatus for testing stiffness of an elongate article along a predetermined testing axis associated therewith, said article having first and second opposed surfaces aligned with a conveying path in a predetermined conveying position, the apparatus comprising:

transport means for moving the article along said path through the apparatus in a conveying direction substantially transverse to said testing axis;

at least one article bearing unit capable of contacting at least said first article surface at two spaced apart portions of the article;

a first deflecting unit including a first working element capable of being disposed in a first substantially static position relative to the article conveying path and cooperating with said article bearing unit for applying a first thrust against a loaded area of the second article surface at an intermediary portion located between the spaced apart portions of the article as it moves transversely through the apparatus, to produce an article deflection of a first magnitude extending along a first deflection axis perpendicular to the conveying direction and the testing axis;

a second deflecting unit including a second working element capable of being disposed in a second substantially static position relative to the article conveying path and cooperating with said article bearing unit for applying a second thrust against a loaded area of said first article surface at the intermediary portion of the article as it further moves transversely through the apparatus, to produce an article deflection of a second magnitude opposite to said first deflection magnitude and extending along a second deflection axis substantially parallel to the first deflection axis;

at least one load measuring unit capable of generating signals indicative of respective magnitudes of said first and second thrusts; and a data processing device for deriving an indication of the stiffness of the article from said first and second opposed deflection magnitudes and said signals.

2. The apparatus according to claim 1, wherein each said working element defines a loading surface extending substantially parallel to the article conveying path when disposed in respective one of said first and second substantially static positions, the dimension of said loading surface parallel to the conveying direction being larger than the transverse dimension of said article at said intermediary portion, so that each said loaded area substantially extends over the whole said transverse dimension while said thrust magnitude indicating signals are generated.

3. The apparatus according to claim 2, wherein each said working element further defines an article feed guiding surface generally extending toward said loading surface according to an acute angle with respect to the article conveying path.

4. The apparatus according to claim 1, further comprising a profile sensing device for providing a signal indicative of the twist characterizing said article, said data processing device being responsive to said twist indicative signal for deriving said indication of the stiffness of the article.

5. The apparatus according to claim 4, wherein said profile sensing device includes at least one presence sensor disposed within the article conveying path.

6. The apparatus according to claim 1, wherein there are first and second article bearing units capable of contacting said first and second article surfaces respectively, said first deflecting unit cooperating with said first article bearing unit for applying said first thrust against the loaded area of the second article surface, said second deflecting unit cooperating with said second bearing unit for applying said second thrust against the loaded area of said first article surface.

7. The apparatus according to claim 6, wherein said first article bearing unit includes a first pair of spaced apart rails defining load bearing surfaces extending substantially parallel to the conveying direction for contacting said first article surface at said spaced apart portions thereof, said load measuring unit including one or more load sensors operatively coupled to said rails.

8. The apparatus according to claim 7, wherein said load measuring unit further includes guide means disposed relative to said article conveying path to set the article on said load bearing surfaces as the article moves through the apparatus.

9. The apparatus according to claim 6, wherein said first and second deflecting units are disposed to respectively face said second and first article surfaces respectively at first and second locations along the article conveying path.

10. The apparatus according to claim 9, wherein said second article bearing unit includes a pair of spaced apart pushing devices disposed to respectively face said second surface of the article at said spaced apart portions thereof.

11. The apparatus according to claim 10, wherein said second article bearing unit includes a second pair of spaced apart rails defining load bearing surfaces extending substantially parallel to the conveying direction for contacting said second article surface at said spaced apart portions thereof, said load measuring unit including a pair of load sensors operatively coupled to said pair of pushing devices.

12. The apparatus according to claim 9, further comprising first and second presence sensors disposed at said first and second locations along the article conveying path for generating control signals whenever the article moves past said first and second locations, said data processing device being responsive to said control signals for deriving said indication of the stiffness of the article.

13. The apparatus according to claim 9, wherein said first article bearing unit includes a first pair of spaced apart rails defining load bearing surfaces extending substantially parallel to the conveying direction for contacting said first article surface at said spaced apart portions thereof, said second article bearing unit including a second pair of spaced apart rails defining load bearing surfaces extending substantially parallel to the conveying direction for contacting said second article surface at said spaced apart portions thereof, said load measuring unit including first and second pairs of load sensors operatively coupled to said first pair of rails and said pair of pushing devices, respectively.

14. The apparatus according to claim 13, wherein said first and second pairs of rails are disposed in a spaced relationship in the conveying direction so their respective load bearing surfaces sequentially receive corresponding said first and second contacted article surfaces when the article moves past said first and second locations along the article conveying path.

15. The apparatus according to claim 14, wherein said load bearing surfaces further extends toward the article intermediary portion transversely to the conveying direction according to respective angles ($\gamma_1$, $\gamma_2$) with reference to said testing axis which are substantially proportional to said first and second deflection magnitudes, respectively, to allow each load bearing surface to follow the shape of corresponding said contacted article surface when the article moves past said first and second locations along the article conveying path.

16. The apparatus according to claim 15, wherein said first and second article bearing units further includes respective first and second pairs of spaced apart guide elements disposed upstream corresponding said first and second pair of rails in an adjacent relationship therewith, for sequentially setting the article on corresponding said load bearing surfaces when the article moves past said first and second locations along the article conveying path.

17. The apparatus according to claim 9, wherein said first deflecting unit further includes a first displaceable mechanism for holding said first working element, said first mechanism being selectively controllable to move the first working element between said first substantially static position relative to the conveying path and a retracted position wherein the first working element is away from the article conveying path to prevent obstruction thereof.

18. The apparatus according to claim 17, wherein said first displaceable mechanism is provided with a first position sensor for generating a first control signal fed to said data processing device whenever said first working element departs from said first substantially static position by a first predetermined overload threshold as a result of a significant departure of said article from the conveying position, said data processing device being responsive to said first control signal to cancel deriving said indication of the stiffness of the article.

19. The apparatus according to claim 18, wherein said second bearing unit includes a pair of spaced apart pushing devices disposed to respectively face said second surface of the article at said spaced apart portions thereof, each said pushing device including a second displaceable mechanism holding a load bearing element, said second mechanism being selectively controllable to move the load bearing element between a working position in contact with said second article surface and a retracted position wherein the load bearing element is away from the article conveying path to prevent obstruction thereof.

20. The apparatus according to claim 19, wherein each said second displaceable mechanism is provided with a second position sensor for generating a second control signal fed to said data processing device whenever said load bearing element departs from said working position by a second predetermined overload threshold as a result of the departure of said article from the conveying position, said data processing device being responsive to said second control signal to cancel deriving said indication of the stiffness of the article.

21. The apparatus according to claim 20, wherein said first displaceable mechanism is further provided with a third position sensor for generating a third control signal fed to said data processing device whenever said first working element substantially departs from said first substantially static position by a third predetermined overload threshold greater than said first overload threshold as a result of the departure of said article from the conveying position, said apparatus further comprising a controller operatively connected to said first and second displaceable mechanisms to provide movement control thereof, said controller being responsive to said third control signal to cause the first displaceable mechanism to move the first working element from said first substantially static position to its retracted position, and to cause each said second displaceable mechanism to move corresponding said load bearing element from its working position to its retracted position.

22. The apparatus according to claim 21, further comprising a presence sensor disposed upstream from said first location for further detecting said article significantly departing from the predetermined conveying position while moving in the conveying direction to generate a fourth control signal, said controller being further responsive to said fourth control signal to cause the first displaceable mechanism to move the first working element from said first substantially static position to its retracted position, and to cause each said second displaceable mechanism to move corresponding said load bearing element from its working position to its retracted position.

23. The apparatus according to claim 22, wherein said second deflecting unit further includes a further displaceable mechanism for holding said second working element, said further mechanism being selectively controllable to move the second working element between said second substantially static position relative to the conveying path and a retracted position wherein the second working element is away from the article conveying path to prevent obstruction thereof, said controller being further responsive to said fourth control signal through the data processing device to cause the further displaceable mechanism to move the second working element from said second substantially static position to its retracted position.

24. The apparatus according to claim 23, further comprising a displacement sensor for generating a signal indicating the displacement along the conveying direction of said article significantly departing from the predetermined conveying position, said data processing device being responsive to said third, fourth and displacement indicating signals to generate a fifth control signal as said article significantly departing from the predetermined conveying position has moved through the apparatus past said second location, said controller being responsive to said fifth control signal to cause the first displaceable mechanism to move the first working element from its retracted position to said first substantially static position, to cause each said second displaceable mechanism to move corresponding said load bearing element from its retracted position to its working position and to cause the further displaceable mechanism to move the second working element from its retracted position to said second substantially static position.

25. The apparatus according to claim 17, wherein said first displaceable mechanism is provided with means for adjusting the first substantially static position of said first working element relative to the article conveying path in a direction perpendicular to said conveying direction and said testing axis.

26. The apparatus according to claim 17, wherein said first displaceable mechanism includes a lever unit provided with a first member having a bearing end pivotally secured to a frame provided on said apparatus, and having a working end pivotally connected to said first working element, said lever unit being further provided with an actuator mounted to said frame and operatively coupled to said first member to selectively exert thereon a compression force to maintain said first working element in said first substantially static position and to provide the movement of said first working element between said first static and retracted positions.

27. The apparatus according to claim 26, wherein said actuator is a pneumatic actuator capable of exerting said compression force within a compliance range, said first working element having a front and rear portions relative to the article conveying direction, said first member working end being pivotally connected to the working element rear portion, said lever unit being provided with a second member having a bearing end pivotally secured to the frame and a working end pivotally connected to the working element front portion, so that said loading surface is maintained parallel to the conveying direction within the compliance range of said pneumatic actuator when said first working element is disposed in said first substantially static position.

28. The apparatus according to claim 27, wherein said pneumatic actuator is provided with means for adjusting the first substantially static position of said working element relative to the article conveying path in a direction perpendicular to said conveying direction and said testing axis.

29. The apparatus according to claim 1, wherein said data processing device compares said article stiffness indication with predetermined reference data for assigning classification data to said article accordingly.

30. The apparatus according to claim 29, further comprising a printing device and a controller operatively connected to said printing device, said printing device being responsive to said assigned classification data through said controller to apply a mark onto the article for indicating the assigned classification data.

31. A method for testing stiffness of an article along a predetermined testing axis associated therewith, said article having first and second opposed surfaces aligned with a conveying path in a predetermined conveying position, the method comprising the steps of:
  i) moving the article along said path in a conveying direction substantially transverse to said testing axis;
  ii) contacting said first article surface at two spaced apart portions of the article while applying a first thrust against a loaded area of said second article surface at an intermediary portion located between the spaced apart portions of the article as it moves transversely along the conveying path, to produce an article deflection of a first magnitude extending along a first deflection axis perpendicular to the conveying direction and the testing axis;

iii) measuring the magnitude of said first thrust;
iv) contacting said second article surface at two spaced apart portions of the article while applying a second thrust against a loaded area of said first article surface at the intermediary portion of the article as it further moves transversely along the conveying path, to produce an article deflection of a second magnitude opposite to said first deflection magnitude and extending along a second deflection axis substantially parallel to the first deflection axis;
v) measuring the magnitude of said second thrust; and
vi) deriving an indication of the stiffness of the article from said first and second opposed deflection magnitudes and said first and second thrust magnitudes.

32. The method according to claim 31, further comprising before said deriving step vi) a step of sensing the profile of said article to provide an indication of the twist characterizing the article, said stiffness indication being derived at said step vi) from said twist indication.

33. The method according to claim 31, wherein said steps ii) and iv) are performed at respective first and second locations along the article conveying path.

34. The method according to claim 33, further comprising simultaneously to said steps ii) and iv), steps of detecting the presence of said article as it moves past said first and second locations prior to perform said step vi).

35. The method according to claim 31, further comprising a step of comparing said article stiffness indication with predetermined reference data for assigning classification data to said article accordingly.

36. The method according to claim 31, wherein each said loaded area substantially extends over the whole transverse dimension of said article while said thrust magnitudes are measured.

* * * * *